(12) United States Patent
Kamler

(10) Patent No.: US 11,565,092 B2
(45) Date of Patent: Jan. 31, 2023

(54) ENDOSCOPIC DILATOR

(71) Applicant: Alpine Medical Devices, LLC, Carmel, CA (US)

(72) Inventor: Jan P. Kamler, Carmel, CA (US)

(73) Assignee: Alpine Medical Devices, LLC, Carmel, CA (US)

( * ) Notice: Subject to any disclaimer, the term of this patent is extended or adjusted under 35 U.S.C. 154(b) by 1003 days.

(21) Appl. No.: 16/291,580

(22) Filed: Mar. 4, 2019

(65) Prior Publication Data
US 2019/0275306 A1 Sep. 12, 2019

Related U.S. Application Data

(60) Provisional application No. 62/639,422, filed on Mar. 6, 2018.

(51) Int. Cl.
*A61M 29/00* (2006.01)
*A61B 1/00* (2006.01)
*A61B 1/273* (2006.01)
*A61B 1/313* (2006.01)
(Continued)

(52) U.S. Cl.
CPC ......... *A61M 29/00* (2013.01); *A61B 1/00135* (2013.01); *A61B 1/00131* (2013.01); *A61B 1/018* (2013.01); *A61B 1/2736* (2013.01); *A61B 1/313* (2013.01); *A61M 29/02* (2013.01);
(Continued)

(58) Field of Classification Search
CPC ...... A61M 29/00; A61B 1/313; A61B 1/3132; A61B 17/02; A61B 17/3421; A61B 17/3439; A61B 17/3462; A61B 1/00131; A61B 1/00135
See application file for complete search history.

(56) References Cited

U.S. PATENT DOCUMENTS

| | | |
|---|---|---|
| 4,726,373 A | 2/1988 | Greengrass |
| 5,916,145 A | 6/1999 | Chu et al. |
| 6,293,909 B1 | 9/2001 | Chu et al. |

(Continued)

FOREIGN PATENT DOCUMENTS

| | | |
|---|---|---|
| CA | 2379670 | 2/2001 |
| CA | 2482969 | 10/2003 |

(Continued)

OTHER PUBLICATIONS

Extended European search report for European patent application No. 19763733.3, dated Nov. 11, 2021, 4 pages.

(Continued)

*Primary Examiner* — Sarah W Aleman
(74) *Attorney, Agent, or Firm* — Mai-Tram D. Lauer; Westman, Champlin & Koehler P.A.

(57) ABSTRACT

A dilator releasably connected with an endoscope to dilate a stricture as the dilator that is releasably connected to a portion of a cylindrical body of the endoscope passes through the stricture. The endoscopic dilator is moveable between an open position and a closed position configured to enable the dilator to be secured to the endoscope. When the dilator is in the closed position, an inner surface or a component on the inner surface of the dilator frictionally secures dilator to the portion of the cylindrical body of the endoscope. When in the open position, the dilator is not frictionally secured to the portion of the cylindrical body of the endoscope.

20 Claims, 27 Drawing Sheets

(51) Int. Cl.
*A61B 1/018* (2006.01)
*A61M 29/02* (2006.01)

(52) U.S. Cl.
CPC . *A61M 2029/025* (2013.01); *A61M 2210/105* (2013.01); *A61M 2210/1053* (2013.01)

(56) References Cited

U.S. PATENT DOCUMENTS

| | | | |
|---|---|---|---|
| 6,334,863 B1 | 1/2002 | Srinivasan | |
| 6,436,119 B1 | 8/2002 | Erb et al. | |
| 6,488,653 B1 | 12/2002 | Lombardo | |
| 6,623,460 B1* | 9/2003 | Heck | A61M 39/06 604/256 |
| 6,953,431 B2 | 10/2005 | Barthel | |
| 7,309,344 B2 | 12/2007 | Bakos et al. | |
| 8,298,134 B2 | 10/2012 | Barthel | |
| 8,371,555 B2* | 2/2013 | Rickerd | A61M 39/0606 604/167.04 |
| 9,510,813 B2* | 12/2016 | Levy | A61B 17/3421 |
| 2004/0059339 A1 | 3/2004 | Roehm, III et al. | |
| 2005/0070949 A1 | 3/2005 | Bakos et al. | |
| 2005/0234304 A1* | 10/2005 | Dewey | A61B 17/3439 600/210 |
| 2006/0004398 A1* | 1/2006 | Binder, Jr. | A61B 17/3417 606/191 |
| 2006/0287574 A1 | 12/2006 | Chin | |
| 2007/0233221 A1 | 10/2007 | Raju | |
| 2009/0048486 A1 | 2/2009 | Surti | |
| 2009/0137870 A1 | 5/2009 | Bakos et al. | |
| 2009/0287050 A1 | 11/2009 | Barthel | |
| 2009/0306472 A1 | 12/2009 | Filipi et al. | |
| 2012/0165916 A1 | 6/2012 | Jordan | |
| 2014/0276869 A1* | 9/2014 | Tatsumi | A61B 17/3421 606/90 |
| 2014/0277059 A1 | 9/2014 | Lam et al. | |
| 2014/0316209 A1 | 10/2014 | Overes et al. | |

FOREIGN PATENT DOCUMENTS

| | | |
|---|---|---|
| CA | 2453743 | 6/2004 |
| CN | 102000389 A | 4/2011 |
| DE | 60311564 | 11/2007 |
| EP | 0178094 | 4/1986 |
| EP | 1202771 | 5/2002 |
| EP | 1430926 | 6/2004 |
| EP | 1494745 | 1/2005 |
| EP | 1647233 | 4/2006 |
| GB | 2164854 | 4/1986 |
| JP | 2003507096 | 2/2003 |
| JP | 2004202236 | 7/2004 |
| JP | 2005522278 | 7/2005 |
| JP | 2006122674 | 5/2006 |
| WO | 0007495 | 2/2000 |
| WO | 03086524 | 10/2003 |
| WO | 2007098416 | 8/2007 |
| WO | 2007117930 | 10/2007 |
| WO | 2007146881 | 12/2007 |
| WO | 2008089424 | 7/2008 |
| WO | 2009021030 | 2/2009 |
| WO | 2012088089 | 6/2012 |
| WO | WO-2018089710 A1 | 5/2018 |

OTHER PUBLICATIONS

Notification of Reasons for Refusal for Japanese patent application No. 2020-570658, dated Dec. 20, 2021, 6 pages.
Office Action from U.S. Appl. No. 16/291,654, dated Jun. 27, 2022, 15 pages.

* cited by examiner

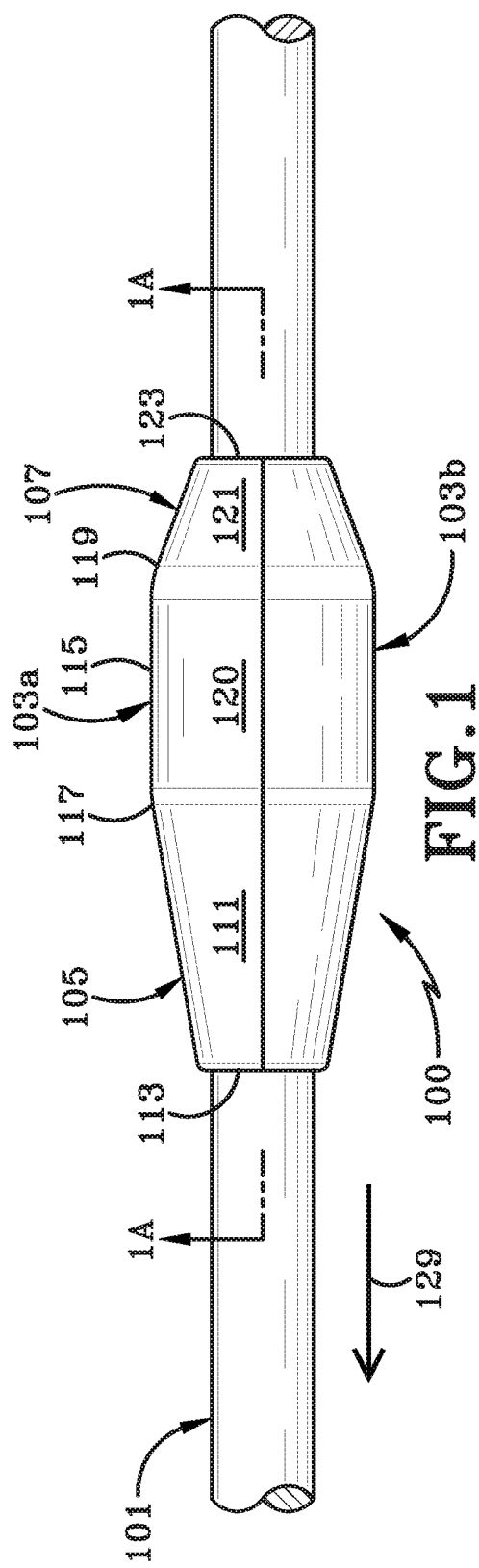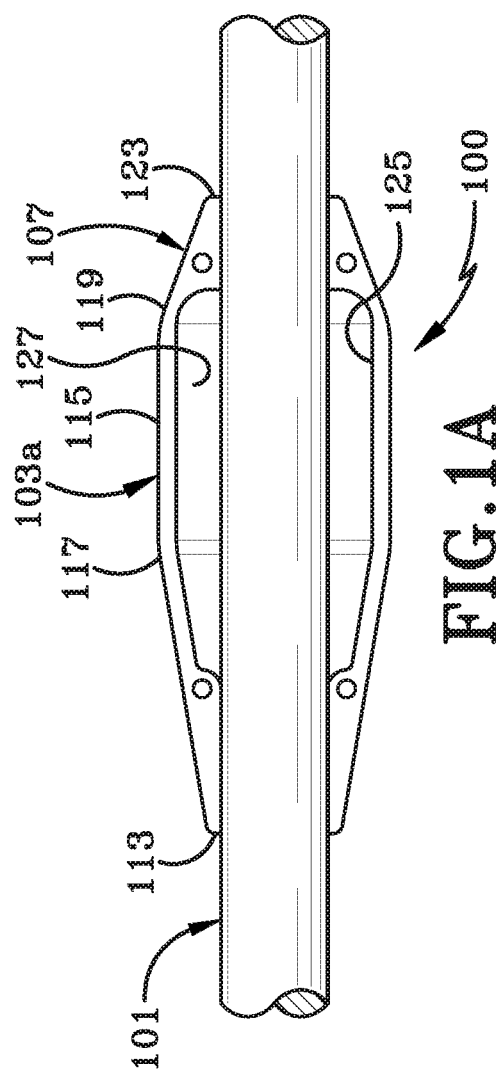

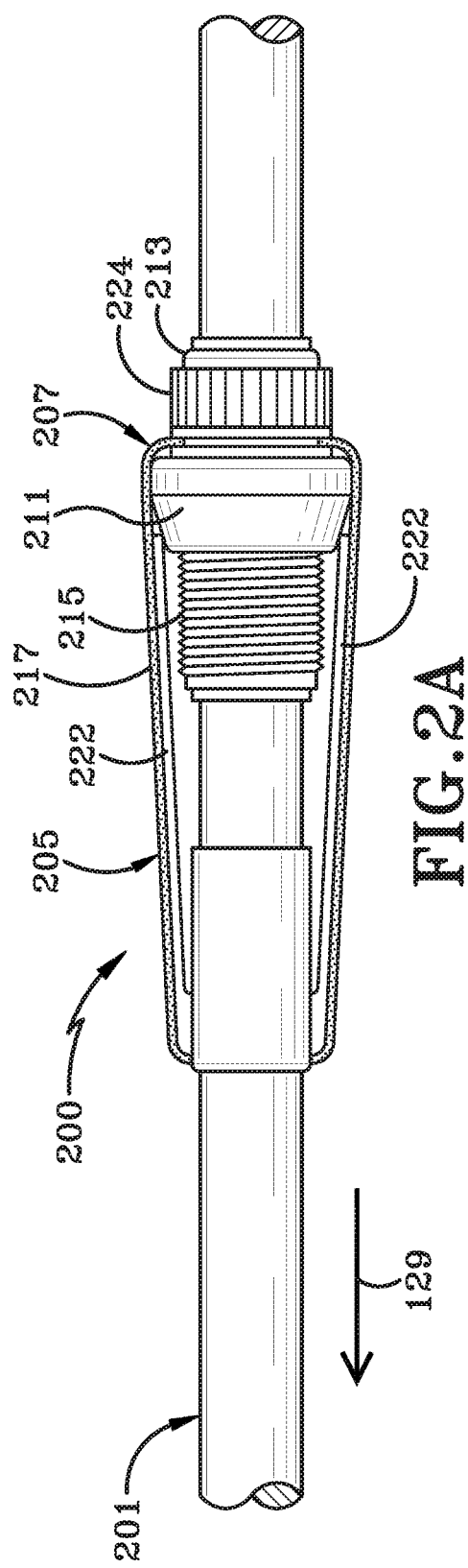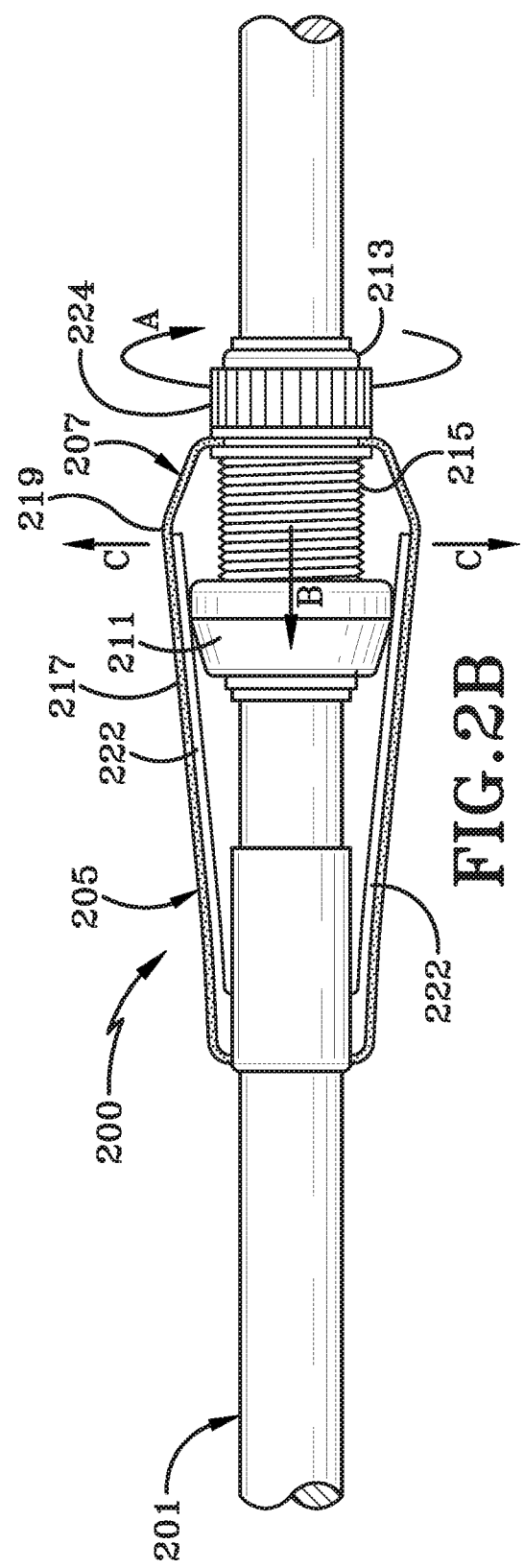

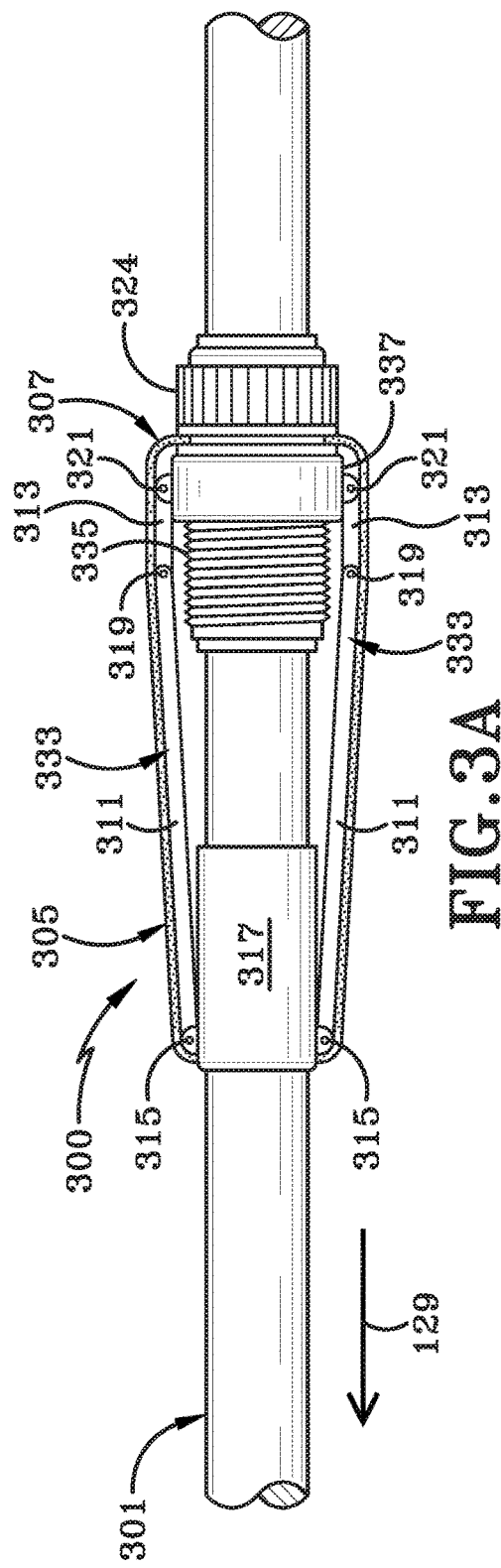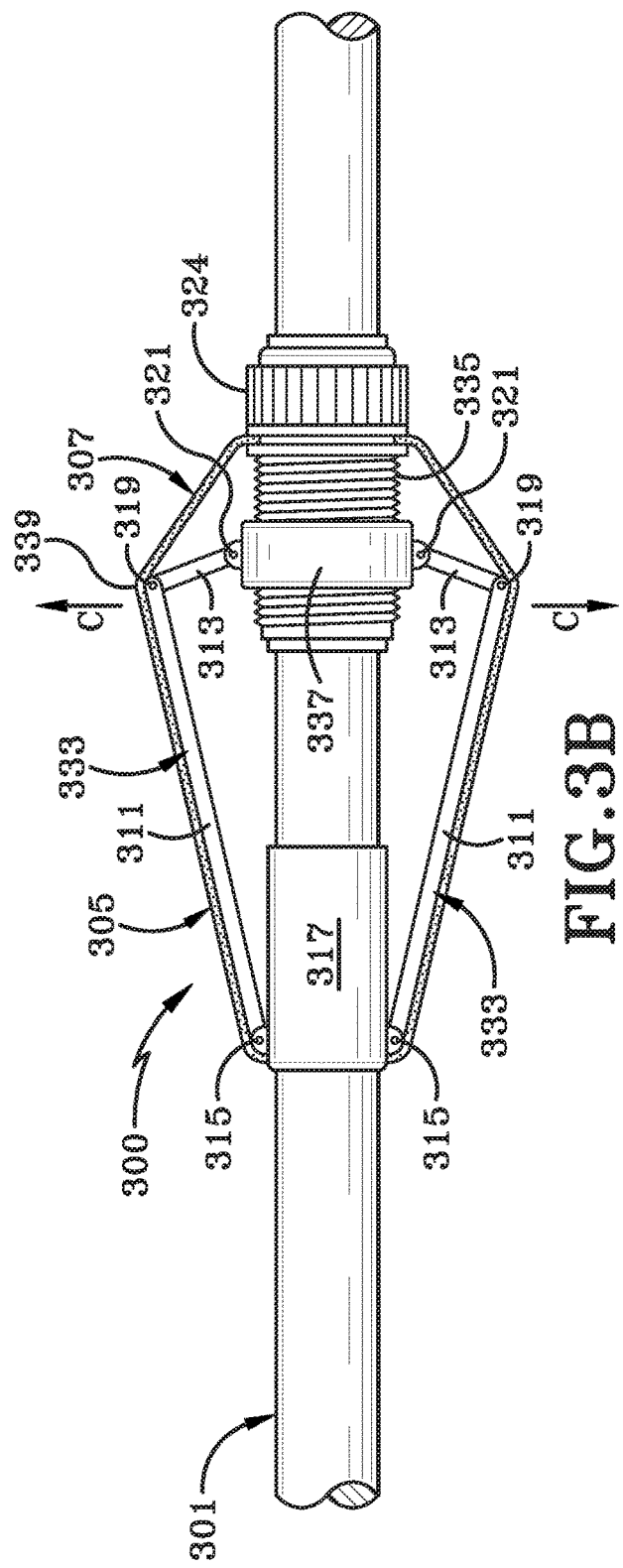

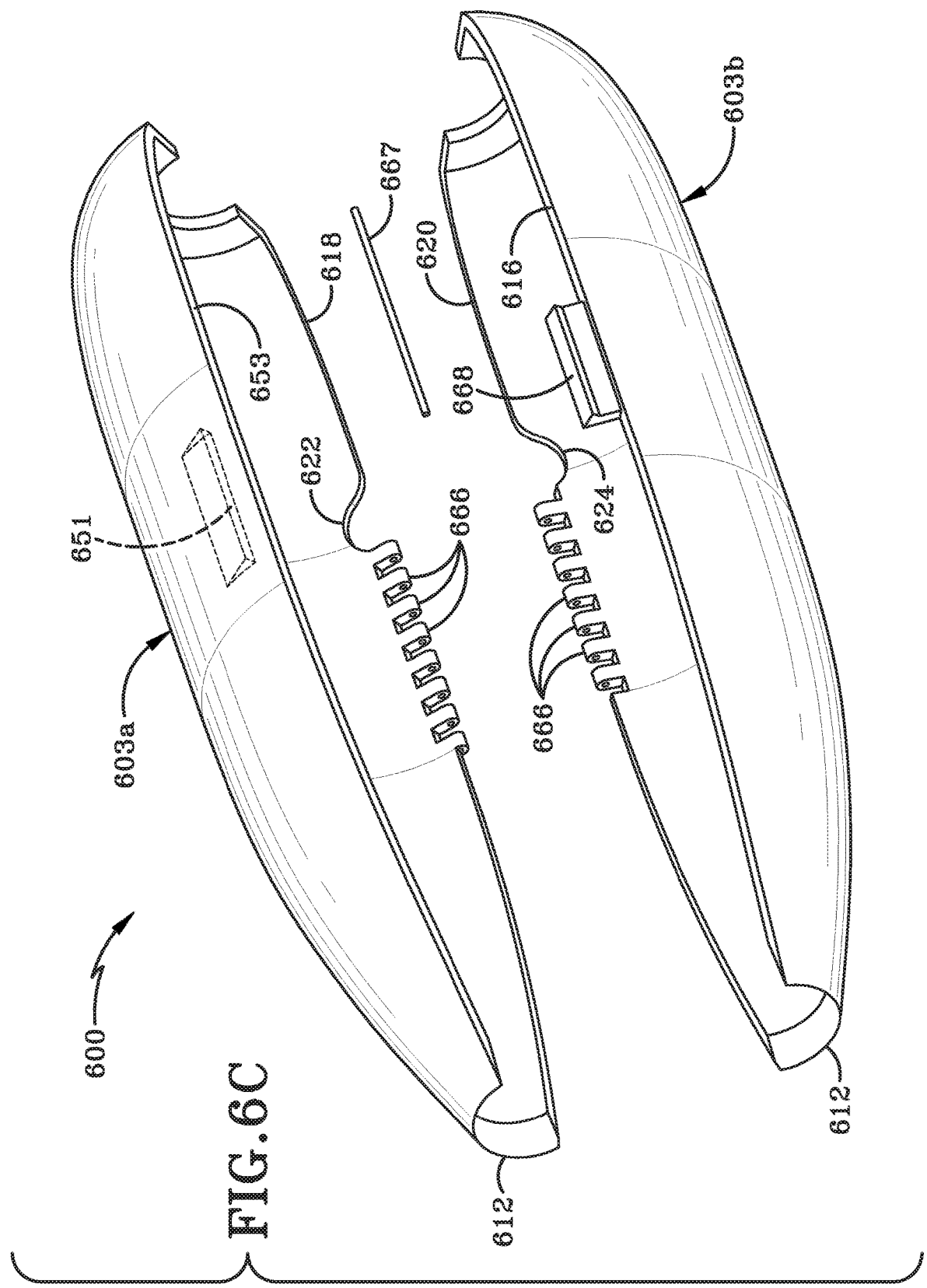

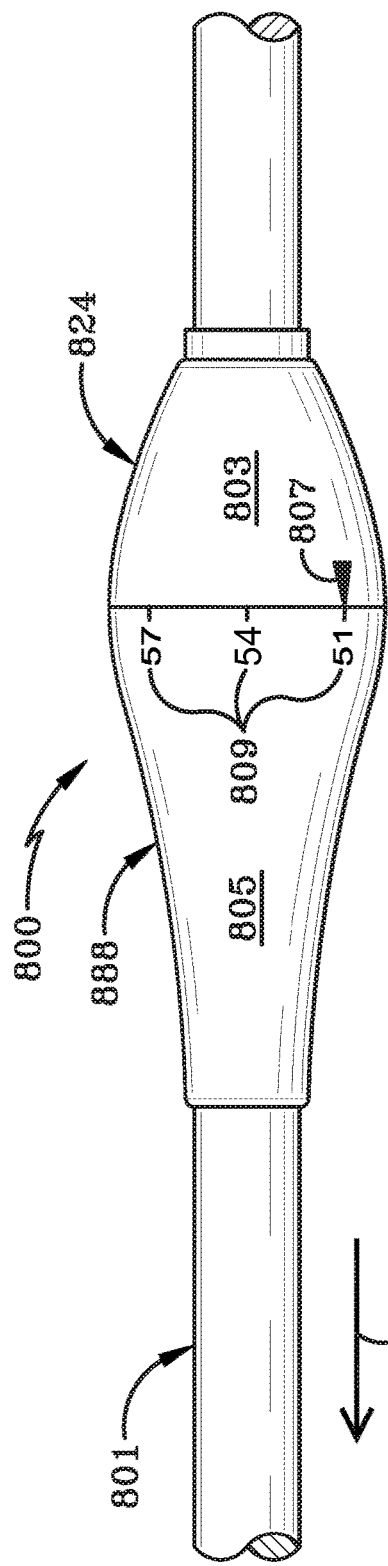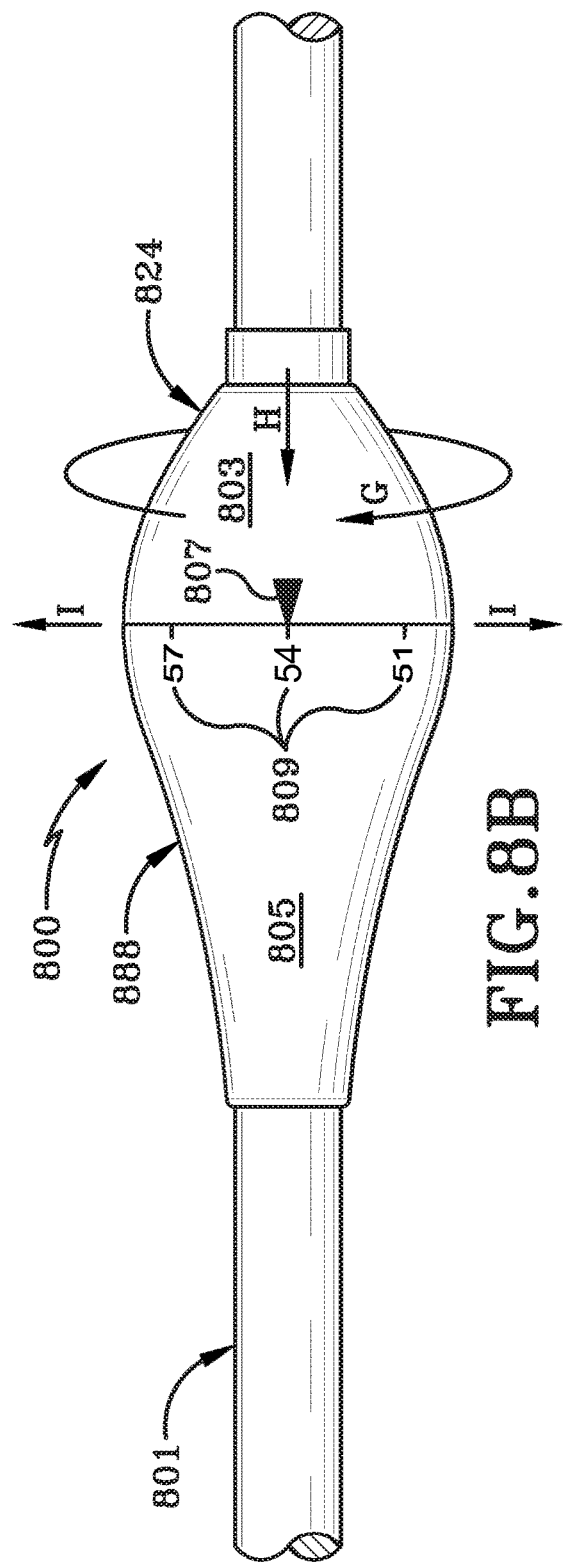

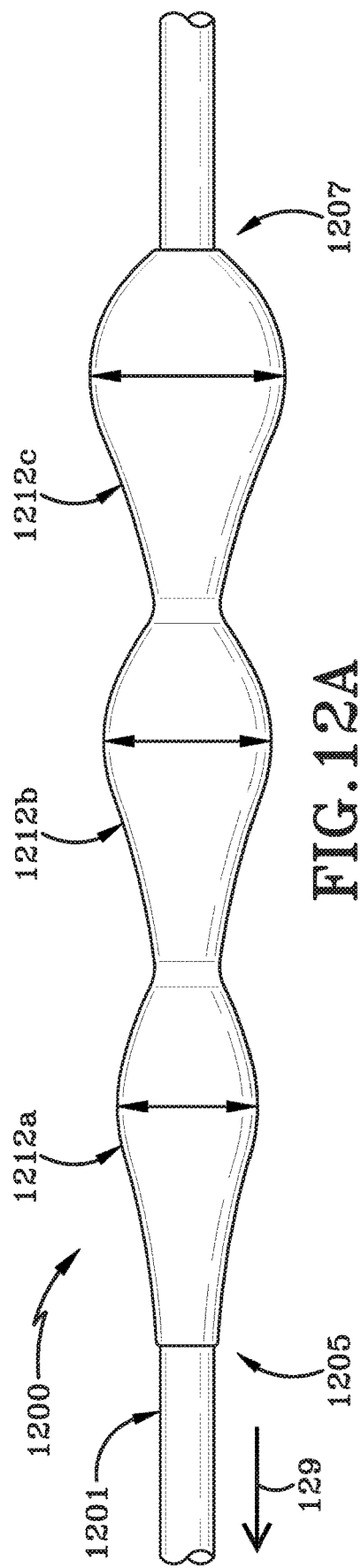
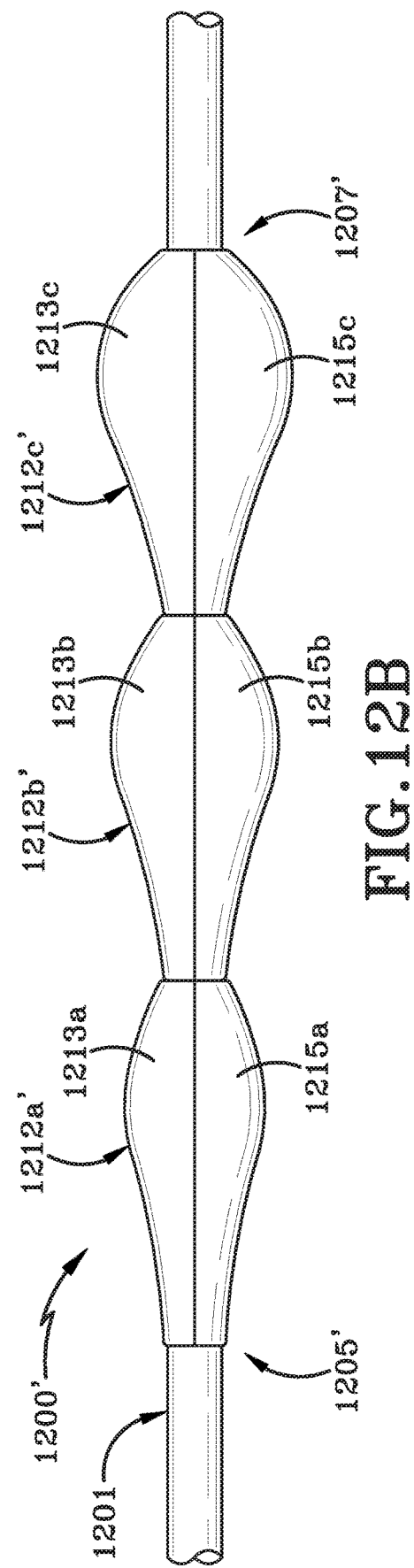

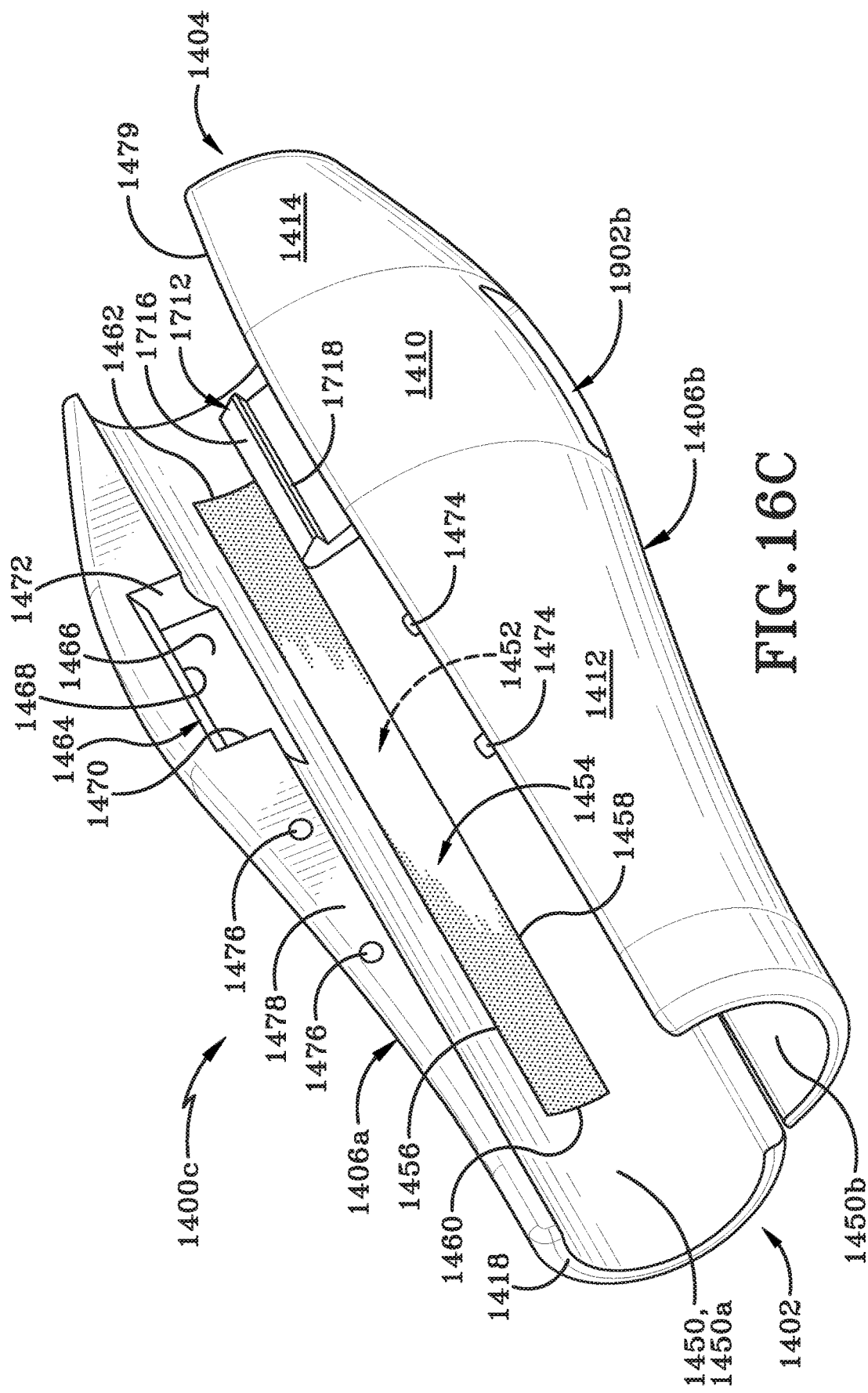

ENDOSCOPIC DILATOR

CROSS-REFERENCE TO RELATED APPLICATION

This application claims the benefit of U.S. Provisional Application Ser. No. 62/639,422, filed Mar. 6, 2018, the disclosure of which is incorporated herein by reference.

TECHNICAL FIELD

Endoscopic dilation is a standard method of treatment of abnormally narrow areas of the digestive tract, called strictures. Strictures can be benign (non-cancerous) or malignant (cancerous). They may involve practically any part of the digestive tract. Endoscopic dilation of benign esophageal strictures is the most frequently performed dilation in daily gastrointestinal endoscopy practice.

BACKGROUND

Endoscopic devices that are used to dilate or stretch esophageal strictures are called dilators. They exert expansive forces against a stricture, which can lead to rupturing or stretching of the stricture. Currently available endoscopic dilators can be divided into two main types. The first type of dilator is a balloon dilator. Balloon dilators are inflatable and may be either one set diameter for a single dilation or adjustable-diameter for sequential expansion and thus sequential dilation. The second type of dilator is a bougie dilator. Bougie dilators are fixed-diameter, pushable dilators.

When using a balloon dilator, the endoscope is inserted into the esophagus and the balloon is pushed through the stricture. Then, under direct visualization, the balloon is inflated, deflated, and the stricture re-inspected to rule out complications. The advantage of balloon dilation is direct visualization of the dilation, single intubation of the esophagus, and no need for cleaning or sterilization because the balloons are designed for a single use. The disadvantage of the balloon dilation is the high cost of the balloon and the lack of tactile sensation and feedback from the stricture resistance during dilation, which can result in perforation of the esophagus.

When using bougie dilators, the endoscope is inserted into the esophagus and, if possible, through the stricture. Then, depending on the type of bougie dilator, a guidewire is left behind after the endoscope is withdrawn (Savary-Guillard type dilator) or the endoscope is withdrawn without the use of a guidewire (Maloney type dilator). In the case of Savary-Guillard dilation, the dilator is then inserted over the guide wire and the stricture is dilated. With the Maloney dilator, the dilator is inserted into the esophagus blindly without the guidance of a guide wire and the stricture is dilated. Savary-Guillard dilation is generally considered a safer procedure because of a higher rate of perforation using the Maloney device. After both types of bougie dilation, the esophagus is usually re-inspected to rule out complications and this requires repeat intubation of the esophagus. The advantage of bougie dilators is the relatively low cost, which involves only the initial purchase of the dilator set and the occasional purchase of new guidewires for use with Savary-Guillard dilators only. Another advantage is the tactile sensation and feedback from the stricture resistance, which improves safety and decreases the risk of perforation. Disadvantages of bougie dilators are the cost of sterilization, risk of infection, soiling of the operating field and risk of trauma to the endoscopic staff caused by a guide wire.

Another disadvantage is repeat intubation of the esophagus for re-inspection of the stricture after dilation. Also, if necessary, the use of multiple dilators for sequential dilation prolongs the procedure and requires more time from the support staff to clean and disinfect the dilators and wires.

SUMMARY

An endoscopic dilator that solves some or all of the problems with currently available dilators is thus desired.

In one aspect, the present disclosure may provide an endoscopic dilator that is configured to attach to an endoscope. The dilator can be conical or tapered and include two or three clamshell-like parts that are snapped around the endoscope. In some embodiments, the two parts can include expandable mechanical elements to help with dilation. Because the dilator is attached to the endoscope, the dilated area can be quickly evaluated with the scope.

In another aspect, an exemplary embodiment of the present disclosure may provide a dilator for connection with an endoscope to dilate a stricture, the dilator comprising: a first segment or part defining a first side of a hinge; a second segment or part defining a second side of the hinge, wherein the first side and the second side of the hinge are coupled together to pivotably connect the first segment and the second segments together, wherein the first segment and the second segment pivot between an open position and a closed position via the hinge, and when the first segment and the second segment are in the open position, a portion of the endoscope is moveable into engagement with one of the first segment/part and the second segment/part, and when the first segment/part and the second segment/part are in the closed position, the first segment and the second segment circumscribe and connect to the portion of the endoscope; wherein when the first segment and the second segment are connected together in the closed position, the dilator includes: a proximal end spaced from a distal end defining a longitudinal axis, wherein the distal end is configured to pass through the stricture before the proximal end; an outer surface extending from the proximal end to the distal end; a distal portion of the outer surface that is tapered relative to the longitudinal axis at a first angle; a proximal portion of the outer surface that is tapered relative to the longitudinal axis at a second angle that is smaller than the first angle, such that the distal portion of the outer surface is longitudinally elongated relative to the proximal portion of the outer surface; an apex of the outer surface intermediate the proximal portion and the distal portion of the outer surface; and an inner surface shaped complementary to an exterior of the endoscope and adapted to circumscribe at least a portion of an exterior of the endoscope.

This exemplary embodiment or another exemplary embodiment may further provide a frustoconical first surface on the distal portion of the outer surface that extends between a first terminal end and the apex; a frustoconical second surface on the proximal portion of the outer surface that extends between a second terminal end and the apex; wherein the frustoconical first surface is longer than the frustoconical second surface. This exemplary embodiment or another exemplary embodiment may further provide a curved first surface on the distal portion of the outer surface that extends between a first terminal end and the apex; a curved second surface on the proximal portion of the outer surface that extends between a second terminal end and the apex; wherein the curved first surface is longer than the curved second surface. This exemplary embodiment or another exemplary embodiment may further provide wherein the curved first surface is concavely curved. This exemplary embodiment or another exemplary embodiment may further provide wherein the curved second surface is convexly curved. This exemplary embodiment or another exemplary embodiment may further provide wherein the curved first surface is convexly curved. This exemplary embodiment or another exemplary embodiment may further provide wherein the apex defines a point between the proximal portion and the distal portion. This exemplary embodiment or another exemplary embodiment may further provide wherein the apex is convexly curved between the proximal portion and the distal portion. This exemplary embodiment or another exemplary embodiment may further provide a first connector on the first segment opposite the hinge; a second connector on the second segment opposite the hinge; wherein the first connector and the second connector effectuate a releasable connection between the first segment and the second segment, and when the dilator is in the open position the first connector and the second connector are disconnected and when the dilator is in the closed position the first connector and the second connector are connected. This exemplary embodiment or another exemplary embodiment may further provide a first recess formed in the inner surface of the first segment; a first insert shaped complementary to the first recess and disposed within the first recess, and the first insert configured to frictionally engage the exterior of the endoscope. This exemplary embodiment or another exemplary embodiment may further provide a second recess formed in the inner surface of the second segment; a second insert shaped complementary to the second recess and disposed within the second recess, and the second insert configured to frictionally engage the exterior of the endoscope when the dilator in the closed position. This exemplary embodiment or another exemplary embodiment may further provide wherein the first recess and the second recess are longitudinally elongated. This exemplary embodiment or another exemplary embodiment may further provide wherein the first recess is rectangular. This exemplary embodiment or another exemplary embodiment may further provide wherein the first recess is offset 180 degrees relative to the longitudinal axis from the second recess when the dilator is in the closed position. This exemplary embodiment or another exemplary embodiment may further provide a component connected to the inner surface that has a higher coefficient of friction relative to the exterior of the endoscope than does the inner surface. This exemplary embodiment or another exemplary embodiment may further provide that the component is spray-on applied to the inner surface. This exemplary embodiment or another exemplary embodiment may further provide a recess formed in the outer surface and a supplemental component for insertion into the recess formed in the outer surface to increase an outer diameter of the dilator when the dilator is in the closed position. This exemplary embodiment or another exemplary embodiment may further provide a high-friction layer disposed between the inner surface of the first segment and an exterior of the endoscope when the dilator is in the closed position. This exemplary embodiment or another exemplary embodiment may further provide wherein the apex is disposed closer to the proximal end of the dilator than to the distal end.

In another aspect, an exemplary embodiment of the present disclosure may provide a dilator releasably connected with an endoscope to dilate a stricture as the dilator that is releasably connected to a portion of a cylindrical body of the endoscope, passes through the stricture; the dilator including a component on or adjacent an inner surface of the dilator to frictionally engage an exterior surface of the portion of the cylindrical body of the endoscope, and the dilator including a first element and a second element that are hinged together to move the dilator between an open position and a closed position configured to enable the endoscope to be positioned between the first element and the second element, wherein when the first element and the second element are in the closed position, the component frictionally secures the dilator to the portion of the cylindrical body of the endoscope and when the first element and the second element are in the open position, the component does not frictionally secure the dilator to the portion of the cylindrical body of the endoscope.

In yet another aspect, an exemplary embodiment of the present disclosure may provide a method comprising providing a first device formed from two parts hinged together that pivot between an open position and a closed position; opening the first device to the open position; disposing an elongated member adjacent an interior surface of one of the two parts, wherein a length of the elongated member extends distally from a distal end of the first device; securing the first device to the elongated member by pivoting the two parts to the closed position while retaining the elongated member between the two parts such that the first device translates relative a longitudinal axis of the elongated member; moving the elongated member and the first device through a lumen formed in a tubular body; approaching a narrowed region of the lumen with a distal end of the elongated member; first, moving the length of the elongated member that extends distally from a distal end of the first device through the narrowed region of the lumen without affecting a diameter of the narrowed region and then moving the first device through the narrowed region of the lumen; dilating the narrowed region of the lumen as the first device passes therethrough to increase a diameter of the narrowed region, wherein the narrowed region has a larger diameter after the first device has been passed therethrough than prior to moving the first device though the narrowed region of the lumen.

This exemplary embodiment of the method or another exemplary embodiment of a method may further provide removing the first device and the elongated member from the lumen; pivoting the two parts from the closed position; and disconnecting the elongated member from the first device. This exemplary embodiment of the method or another exemplary embodiment of a method may further provide wherein prior to disposing the elongated member adjacent the interior surface of one of the two parts in the open position the method comprises inserting the elongated member in the lumen formed in the tubular body without the first device connected to the elongated member; inspecting the narrowed region of the lumen; extracting the elongated member from the lumen, and then disposing the elongated member adjacent the interior surface of one of the two parts. This exemplary embodiment of the method or another exemplary embodiment of a method may further provide securing the first device to the elongated member in a range from about 20 cm to about 30 cm from a terminal end of the elongated member. This exemplary embodiment of the method or another exemplary embodiment of a method may further provide dilating the narrowed region to have a diameter in a range from about 42 French to about 60 French after having passed the first device therethrough. This exemplary embodiment of the method or another exemplary embodiment of a method may further provide increasing an external diameter of the first device after having passed through the narrowed region at least once. This exemplary embodiment of the method or another exemplary embodiment of a method may further provide attaching a cover to an outer surface of the first device to increase the external diameter of the first device. This exemplary embodiment of the method or another exemplary embodiment of a method may further provide expanding an outer surface of the first device to increase the external diameter of the first device, wherein expanding the outer surface is accomplished by rotating a threaded component about a longitudinal axis of the first device to cause linear translation thereof to push the outer surface radially outward relative to the longitudinal axis. This exemplary embodiment of the method or another exemplary embodiment of a method may further provide dilating the narrowed region a second time after having increased the external diameter of the first device.

In yet another aspect, an exemplary embodiment of the present disclosure may provide a method comprising inserting a portion of an endoscope into an esophagus of a patient; passing a distal end of the endoscope through the esophagus towards a stomach of the patient; approaching the distal end of the endoscope towards a stricture positioned in the esophagus before the stomach; inspecting the stricture and approximating a diameter of the stricture; extracting a portion of the endoscope from the esophagus while leaving the distal end of the endoscope intubated within the esophagus; connecting a dilator to the extracted portion of the endoscope while the distal end of the end of the endoscope remains intubated within the esophagus; passing the dilator connected to the endoscope through the esophagus; for a second time, approaching the distal end of the endoscope towards the stricture; passing the distal end of the endoscope through the stricture and into the stomach; passing the dilator through the stricture and into the stomach to dilate the stricture to have a greater diameter than prior to the dilator passing therethrough, wherein as the dilator is passed through the stricture, the distal end of the endoscope advances farther into the stomach; extracting the dilator through the stricture in an opposite direction; for a second time, inspecting the stricture after having been dilated by the dilator; confirming that the stricture has been dilated to a preferred diameter; and removing the dilator and endoscope from the esophagus. This exemplary embodiment of the method or another exemplary embodiment of a method may further provide that the connecting of the dilator to the extracted portion of the endoscope includes moving a first part of the dilator to an open position; positioning the extracted portion of the endoscope adjacent an inner surface of the dilator; moving the first part of the dilator to a closed position; and releasably securing the dilator in the closed position. This exemplary embodiment of the method or another exemplary embodiment of a method may further provide that the connecting of the dilator to the extracted portion of the endoscope further includes positioning the dilator a distance in a range from about 20 cm to about 30 cm from the distal end of the endoscope. This exemplary embodiment of the method or another exemplary embodiment of a method may further provide wherein connecting the dilator to the extracted portion of the endoscope further includes contacting ridges formed in a distal end of the first part with an exterior surface of the extracted portion of the dilator. This exemplary embodiment of the method or another exemplary embodiment of a method may further provide wherein connecting the dilator to the extracted portion of the endoscope further includes: releasably securing the first part to a second part of the dilator via a snap-fit connection. This exemplary embodiment of the method or another exemplary embodiment of a method may further provide wherein connecting the dilator to the extracted portion of the endoscope further includes: aligning a first high-friction component adjacent or on the inner surface of the first part 180 degrees from a second high-friction component adjacent or on an inner surface of a second part of the dilator. This exemplary embodiment of the method or another exemplary embodiment of a method may further provide wherein connecting the dilator to the extracted portion of the endoscope further includes pivoting the first part about a hinged relative to a second part to releasably secure the dilator in the closed position. This exemplary embodiment of the method or another exemplary embodiment of a method may further provide wherein connecting the dilator to the extracted portion of the endoscope further includes minimizing an internal diameter of the dilator measured between complementary inner surfaces on the first part and a second part, wherein the internal diameter is minimized in the closed position and in the inner surfaces are in direct contact with an exterior surface of the extracted portion of the endoscope. This exemplary embodiment of the method or another exemplary embodiment of a method may further provide wherein connecting the dilator to the extracted portion of the endoscope further includes frictionally engaging the inner surface of the dilator to an exterior surface of the extracted portion of the endoscope. This exemplary embodiment of the method or another exemplary embodiment of a method may further provide wherein connecting the dilator to the extracted portion of the endoscope further includes frictionally engaging a component formed from a different material than the first part of the dilator with the exterior surface of the extracted portion of the dilator. This exemplary embodiment of the method or another exemplary embodiment of a method may further provide passing an apex of an outer surface of the dilator through the stricture, wherein the apex is disposed a distance in a range from about 20 cm to about 30 cm from the distal end of the endoscope. This exemplary embodiment of the method or another exemplary embodiment of a method may further provide wherein if the stricture has not been dilated to the preferred diameter, then removing the dilator and the portion of the endoscope from the esophagus of the patient while leaving the distal end of the endoscope intubated within the esophagus; adjusting an external diameter of the dilator while the dilator is outside of the esophagus; and moving the dilator through the stricture for a second time after having the external diameter adjusted. This exemplary embodiment of the method or another exemplary embodiment of a method may further provide wherein adjusting the external diameter of the dilator while the dilator is outside of the esophagus includes attaching a first cover to an outer surface of a first part of the dilator. This exemplary embodiment of the method or another exemplary embodiment of a method may further provide wherein adjusting the external diameter of the dilator while the dilator is outside of the esophagus further includes attaching a second cover to an outer surface of a second part of the dilator. This exemplary embodiment of the method or another exemplary embodiment of a method may further provide wherein adjusting the external diameter of the dilator while the dilator is outside of the esophagus includes increasing the external diameter of the dilator by rotating a threaded component around an axis to translate the threaded component coupled, at least indirectly, to an outer surface of the dilator.

BRIEF DESCRIPTION OF THE SEVERAL VIEWS OF THE DRAWINGS

A sample embodiment of the disclosure is set forth in the following description, is shown in the drawings and is particularly and distinctly pointed out and set forth in the appended claims. The accompanying drawings, which are fully incorporated herein and constitute a part of the specification, illustrate various examples, methods, and other example embodiments of various aspects of the disclosure. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

FIG. 1 depicts shows an exemplary endoscopic dilator in accordance with the present disclosure.

FIG. 1A is a longitudinal side elevation view of the endoscopic dilator of FIG. 1 having one part of the endoscopic dilator removed.

FIG. 2A is a side elevation view of another embodiment of an endoscopic dilator shown in a first or neutral position.

FIG. 2B is a side elevation view of the endoscopic dilator of FIG. 2A shown in a second or expanded/dilating position.

FIG. 3A is a side elevation view of another embodiment of an endoscopic dilator shown in a first or neutral position.

FIG. 3B is a side elevation view of the endoscopic dilator of FIG. 3A shown in a second or expanded/dilating position.

FIG. 6C is an exploded perspective view of the endoscopic dilator of FIG. 6A.

FIG. 8A is a side elevation view of another exemplary endoscopic dilator that varies its outer diameter in response to a rotational action and this endoscopic dilator shown in a home or neutral position having its narrowest possible maximum diameter.

FIG. 8B is a side elevation view of the exemplary endoscopic dilator of FIG. 8A after having its outer diameter increased in response to a rotational action.

FIG. 12A shows another exemplary endoscopic dilator formed from a single member having enlarged diameters aligned in series.

FIG. 12B depicts another exemplary embodiment of a plurality of dilators aligned in series.

FIG. 16C is a perspective view of a dilator having a high friction component on the inner surface and a substantially smooth inner surface near the distal and proximal ends, and the dilator shown in an open position.

Similar numbers refer to similar parts throughout the drawings.

DETAILED DESCRIPTION

Figure 4A:
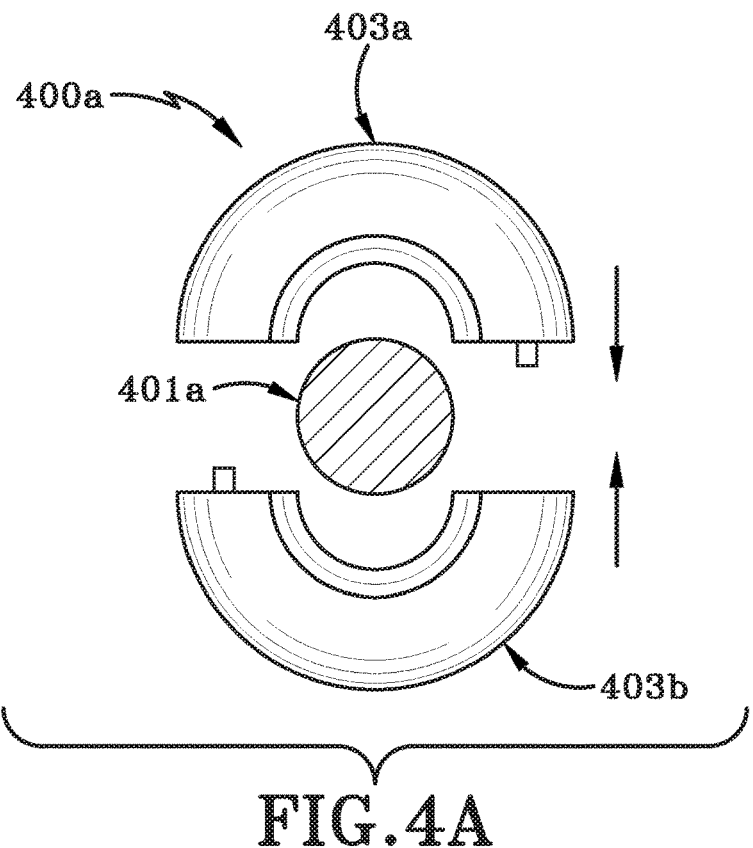
FIG. 4A is a diagrammatic end view of another endoscopic dilator formed from two parts that are removably connectable together in approximate 180 degree segments around an endoscope.

Described herein is an endoscopic dilator. One exemplary embodiment of a dilator is shown generally as 100 is seen in FIG. 1 and FIG. 1A. The dilator 100 includes two parts 103a, 103b configured to snap together around the shaft of an endoscope 101. Notably, the term "parts" as used herein also refers to the term "side segments". The dilator 100 is tapered at both the distal (insertion) end 105 and proximal end 107 with a greater-length taper at the distal end 105 than the proximal end 107. The tapers can form conical distal and proximal ends 105, 107. The maximum outer diameter of the dilator 100 can range from 42 French to 60 French measure through a portion located between the distal end 105 and the proximal end 107, or measured at a point where the conical portions meet. Further, the dilator 100 can be between about five to ten centimeters long. In some embodiments, the dilator 100 can be made of plastic or rubber. However, other materials are entirely possible without departing from the scope of the present disclosure. Further, the parts 103a, 103b can be clamp together tightly, for example with hinges, pins, or straps to fixedly attach to the endoscope until release.

Each part 103a or 103b of dilator 100 may be a unibody that is integrally extruded, molded, printed, or additively manufactured, removably machined, or formed as a unitary, monolithic member substantially fabricated from a substantially rigid or semi-rigid, manmade, material. In one example, polymers, such as hardened plastics, may form a substantial majority of the components or elements used to fabricate the part 103a or 103b of dilator 100 and the various components integrally formed, molded, or extruded therewith. The part 103a or 103b of dilator 100 should withstand typical endoscopic intubation forces from a gastroenterologist maneuvering the part 103a or 103b of dilator 100 through a bodily cavity, organ, or bodily tissue of a patient. While it is contemplated that the part 103a or 103b of dilator 100 and its additional components described herein are uniformly and integrally extruded, molded, or formed, it is entirely possible that the components of the tool body be formed separately from alternative materials as one having routine skill in the art would understand. In another example, the part 103a or 103b of dilator 100 may be formed from an elastomeric material or rubber material configured to withstand slight deformation upon impact or bending by the operator (i.e., a gastroenterologist). Furthermore, while the components of the part 103a or 103b of dilator 100 are discussed below individually, it is to be clearly understood that the components and their corresponding reference elements of the tool body are portions, regions, or surfaces of the body and all form a respective element or component of the unitary part 103a or 103b of dilator 100. Thus, while the components may be discussed individually and identified relative to other elements or components of the tool body, in this exemplary embodiment, there is a single tool body having the below described portions, regions, or surfaces.

With continued reference to FIG. 1 and FIG. 1A, dilator 100 may alternatively be designed to releasably connect with two parts 103a, 103b. Thus, it is not required that the pieces snap together. However, any releasable connection may suffice. Further, the releasable connection may be accomplished by a first pair of connectors on one side of the dilator and a second pair of connectors on the other side of the dilator approximately 180 degrees from the first pair of connectors. When parts 103a, 103b are connected together to form dilator 100, the distal end 105 may define a collective conical outer surface 111 extending from a distal end wall 113 proximately towards an apex region 115 of the maximum outer diameter of the collective dilator 100. In one particular embodiment, the maximum outer diameter measured through the apex of the dilator 100 is in a range from about 42 French to about 60 French. Collectively, parts 103a, 103b form a portion of the outer surface of dilator 100 when connected together. In one particular embodiment, the inner surface of the parts 100a, 100b may be conical and define an inner surface 125 that circumscribes the endoscope 101.

FIG. 1 and FIG. 1A depict that the apex region 115 is a generally cylindrical portion extending from the proximal end 117 of the distal section 105 to the distal end 119 of the proximal section 107. While the apex region 115 of the dilator 100 is shown as having a cylindrical wall of constant diameter, it is to be understood that, and as shown in other embodiments, the apex region 115 may have a convex outer surface. Proximal section 107 may define a frustoconical outer surface 121 collectively by the parts 103a, 103b releasably connected together. Conical outer surface 111 of the distal end 105 may be a frustoconical outer surface that is substantially smooth and continuous between the distal end wall 113 and the apex 115. Apex region 115 defines an outer surface 120 that is continuous and contiguous and uninterrupted with the outer surface 111. Conical outer surface 121 of the proximal end 107 may be a frustoconical outer surface that is substantially smooth and continuous between the distal portion 119 of the proximal section 107 and a proximal end wall 123 and the apex 115.

The tapering angle of the proximal section 107 may be steeper and shorter than that of the distal section 105. Stated otherwise, with respect to a longitudinal axis of the endoscope 101, outer surface 121 of the proximal end 107 tapers at a greater angle than that of the outer surface 111 of the distal end 105. In one particular embodiment, the frustoconical outer surface 121 of the proximal end 107 tapers at an angle relative to the longitudinal axis of the endoscope 101 in a range from about 15° to about 30°. The frustoconical outer surface 111 of the distal end 105 tapers at an angle in a range from about 10° to about 20° relative to the longitudinal axis of the endoscope 101. In some embodiments, the proximal end 107 and the distal end 105 may smoothly transition to be conformal with the outer surface of the endoscope 101 instead of having the end walls 113, 123 defined by the thickness of the part 103a, 103b.

The inner surface 125 of each respective part 103a, 103b defines an interior cavity 127 that is configured to receive the endoscope 101 therein. In one particular embodiment, the cavity 127 defined by the parts 103a, 103b may leave an interior volume filled with air when the parts 103a, 103b are releasably connected to each other around the body of the endoscope 101. In other particular embodiments, the interior surface of the respective parts 103a, 103b may be complementary in shape to the body of the endoscope 101 such that a continuous contact is established between the inner surface of the respective parts 103a, 103b and the cylindrical body of the endoscope 101. Stated otherwise, the inner surface 125 may be circular in cross section having a radius, diameter, and curvature that equals or closely approximates an exterior surface of the endoscope body.

When dilator 100 is connected to the endoscope 101, the dilator is configured to be inserted or intubated into a lumen of a body part, such as an esophagus in the distal direction as indicated by insertion arrow 129 (i.e., insertion direction 129).

Another embodiment of an endoscopic dilator 200 attachable to an endoscope 201 is shown in FIGS. 2A-2B. The dilator 200 is an adjustable diameter dilator 200. Like dilator 100, the dilator 200 has a tapered distal end 205 and can be in any of the shapes described above with respect to the fixed dilators having tapered ends. The taper 205 is formed by a plurality of compliant bars 222 that are molded or otherwise connected onto the device 200. Further, the proximal end 207 has a rotatable knob 224 or nut attached to the bars 222. As the knob 224 is rotated, a wedge nut 211 can be driven under the bars 222 at the proximal ends thereof to cause the dilator 200 to radially expand from the proximal end 207 (i.e., creating a greater taper angle from the proximal end 207 to the distal end 205), as shown in the change from the unexpanded neutral state or position (FIG. 2A) to the expanded state or position (FIG. 2B).

With continued reference to FIG. 2A and FIG. 2B, the diameter of the dilator 200 is adjustable that is effectuated by a collar or sleeve 213 that is rotatably connected to the outer surface of the tubular body of endoscope 201. In one particular embodiment, the sleeve 213 may be joined to the outer surface of the body and formed with external threads 215 such that rotation of the knob 224 effectuates the wedge nut 211 to rotate around the longitudinal axis of the endoscope 201 and move longitudinally towards the distal end 205 along the threads 215. Upon rotation of the knob 224 (as indicated by Arrow A), the threads 215 move the wedge nut 211 distally, as indicated by Arrow B, to flare out the bars 222 and expand the diameter of the outer surface of dilator 200, as indicated by Arrow(s) C. The outer surface of dilator 200 may be a conical section 217 extending from the distal end 205 to the proximal end 207. In this particular embodiment, proximal end 207 is slightly tapered or otherwise transitions towards the knob 224. The apex 219 of dilator 200 would be located at the point at which the proximal ends of bars 222 are below or interior to the outer surface of the conical section 217. Knob 224 may further be delineated with one or a plurality of indicators to identify the maximum diameter of the outer surface of dilator 200 such that it is variable in a range from 42 French to 60 French. When the wedge nut 211 is located at its most proximal position, the maximum diameter of dilator 200 may be at the minimum of the range, such as 42 French. Then, upon rotation and the fully distal translation of the wedge nut 211 may be associated with the maximum diameter of the outer surface of dilator 200 at about 60 French. Stated otherwise, when the wedge nut 211 is at its most distal position, as shown in FIG. 2B, the outer surface of dilator 200 is at its maximum diameter or 60 French and when the wedge nut 211 is at its most proximal position, the outer diameter of the dilator 200 is at its minimum diameter, or about 42 French.

FIG. 3A and FIG. 3B depicts another embodiment of a dilator 300 with an adjustable diameter shown positioned around an endoscope 301. Dilator 300 is similar to dilator 200 except that the bars 222 are replaced with expandable linkages 333. As the knob 324 is turned, a proximal connector 337 attached to the linkages 333 can be moved distally along the screw or threads 335, thereby causing the linkages 333 to compress and expand radially to form a greater taper from the proximal end 307 to the distal end 305 (as shown in the change from FIG. 3A to FIG. 3B).

As depicted in FIGS. 3A and 3B, the linkages 333 extend from distal end 305 to the proximal end 307. Linkages 333 may include a plurality of pivot points that enable the linkages 333 to flare outwardly in response to the connector or nut 337 moving longitudinally or translating along the length of the threaded screws 335 in the distal direction. Thus, as the connector or nut 337 translates distally from its proximal position, the linkages 333 begin to flare outwardly, as indicated by Arrow C, to create a larger outer diameter measured through the apex 339 of the linkages 333. In one particular embodiment, each linkage 333 includes a first arm 311 and a second arm 313. The first arm 311 may be associated with a pivot connection 315 with a connector 317 defining the distal end 305 and an intermediate pivot point 319 connected with a second arm 313. The second arm 313 may then extend proximally from the intermediate pivot point 319 to a pivot connection 321 with the nut or connector 337. In one particular embodiment, the first arms 311 are longer than the second arms 313. More particularly, the first arms 311 may be in a range from three to seven times longer than the second arms 313.

FIG. 4A depicts another embodiment of a dilator 400a that can include two parts 403a, 403b (i.e., first side segment 403a and second side segment 403b) that clamp together around the tubular body of an endoscope 401a. For example, each part 403a, 403b can extend approximately 180 degrees around the circumference of the scope 401a.

With continued reference to FIG. 4A, dilator 400a comprising two parts 403a, 403b may have a substantially continuously curved outer surface that is only slightly interrupted by the parting line or union of the two parts 403a, 403b. The distal end of dilator 400a may be narrowed towards the endoscope 401a and extend proximally in a concavely curved manner to a transition point where the outer surface of each respective part 403a, 403b transitions into a convexly curved outer surface. The convexly curved outer surface extends proximately towards an apex that is arcuately curved. From the apex, the outer surface continues in a convexly curved manner and tapers downwardly towards a proximal portion of the endoscope 401a. In the dilator 400a, little to no portions of the outer surface of dilator 400a are flat when viewed in cross-section. The inner surface of dilator 400a may be concavely curved and conformal with the cylindrical outer surface of endoscope 401a.

Figure 4B:
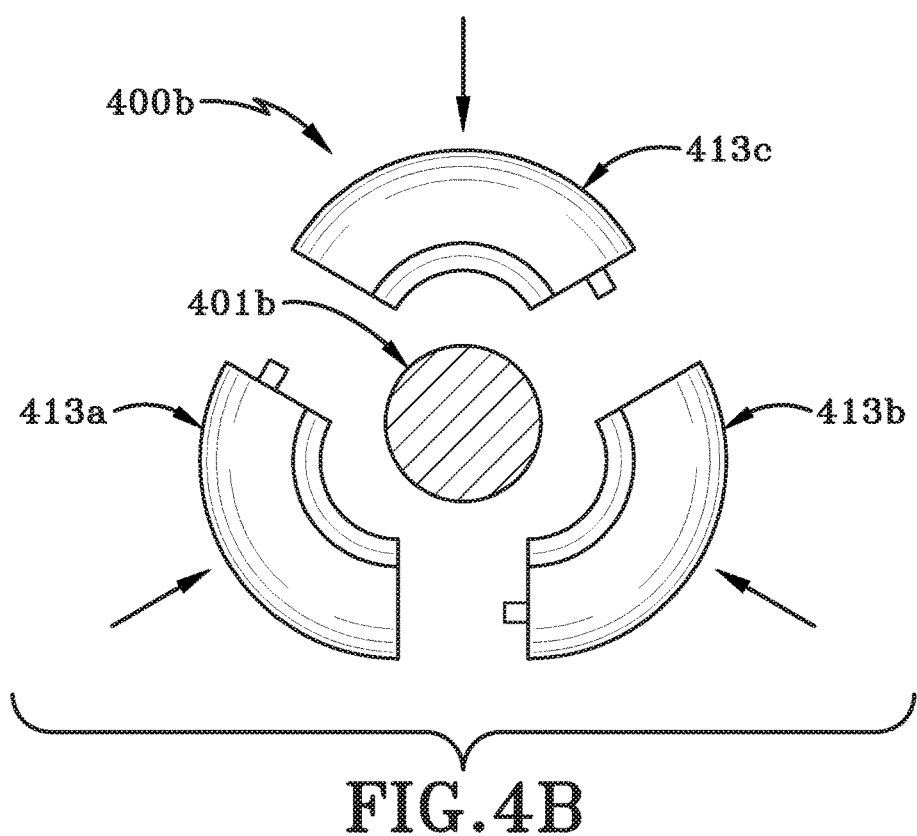
FIG. 4B is a diagrammatic end view of another endoscopic dilator formed from three parts that are removably connectable together in approximate 120 degree segments around an endoscope.

FIG. 4B depicts another exemplary dilator 400b that can include three or more parts 413a, 413b, 413c that clamp together around the scope 401b. For example, each part 413a, 413b, 413c can extend approximately 120 degrees around the circumference of the scope 401b.

As depicted in FIG. 4B, dilator 400b similarly forms a continuously curved outer surface from the parts 413a, 413b, 413c releasably connected together to circumscribe the outer surface of the endoscope body 401b, wherein the curved outer surface is only slightly interrupted by a parting line or union of the respective parts. Similar to dilator 400a, dilator 400b includes a tapered distal end that is slightly concavely curved and extends proximately through a transition point to thereby define a convex outer surface that extends proximately towards an apex that is arcuately convexly curved. From the arcuately curved apex, the outer surface of dilator 400b tapers in a convexly curved manner towards the proximal end of the dilator 400b.

Figure 5A:
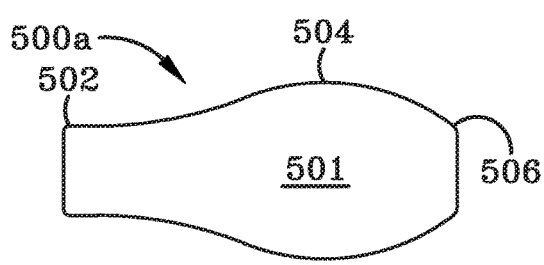
FIG. 5A is a diagrammatic side elevation view of a profile of one exemplary endoscopic dilator in accordance with another as aspect of the present disclosure.

As shown in FIGS. 5A-5J, a dilator as described herein can have a variety of shapes. For example, as shown in FIG. 5A, the dilator 500a can have a smooth tapered formation. More particularly, FIG. 5A depicts the profile of dilator 500a. Dilator 500a includes a continuously curved outer surface 501. The outer surface 501 of dilator 500a is concavely curved from its distal end 502 and transitions to a convexly curved apex 504. From the convexly curved apex 504, the outer surface of dilator 500a extends proximately in a convexly curved manner and tapers downwards to its proximal end point 506 that would transition smoothly to the outer surface of the cylindrical body of an endoscope to which dilator 500a is configured to attach.

Figure 5B:
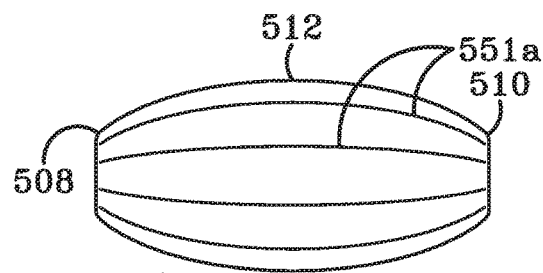
FIG. 5B is a diagrammatic side elevation view of a profile of another exemplary endoscopic dilator in accordance with another as aspect of the present disclosure.

As shown in FIG. 5B, the dilator 500b can have an "olive" shape, e.g., with one or two exterior ridges 551a therein. More particularly, FIG. 5B depicts dilator 500b that has an arcuately curved outer surface that is substantially convex between the distal end 508 and the proximal end 510. Distal end 508 of dilator 500b convexly curves and extends proximally towards the apex 512 of the dilator 500b. The apex 512 of dilator 500b is convexly curved and defines the maximum diameter thereof which is in a range from about 42 French to about 60 French. From the apex 512 of dilator 500b, the outer surface extends in a convexly curved manner from the apex 512 towards the proximal end 510 where it transitions smoothly with the outer surface of the endoscope.

Figure 5C:
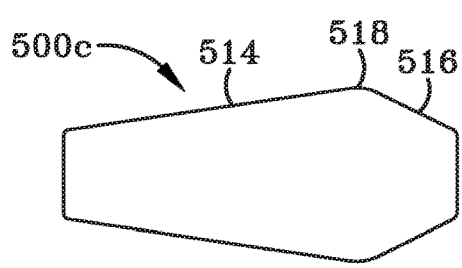
FIG. 5C is a diagrammatic side elevation view of a profile of another exemplary endoscopic dilator in accordance with another as aspect of the present disclosure.

As shown in FIG. 5C, the dilator 500c can be conical. More particularly, FIG. 5C depicts dilator 500c as having two frustoconical sections 514, 516 defining the distal outer surface and the proximal outer surface of dilator 500c, respectively. The frustoconical sections 514, 516 defining the outer surface of the dilator 500c are flat when viewed in cross-section and transition at an apex point 518 defined by the distal conical surface and the proximal conical surface, respectively. While the apex 518 is defined by a point of dilator 500c, it is possible that the point would be rounded so as to effectuate an atraumatic passage through a stricture in the esophagus.

Figure 5D:
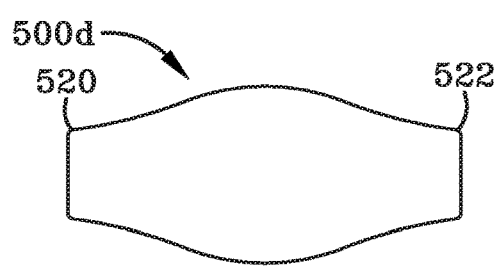
FIG. 5D is a diagrammatic side elevation view of a profile of another exemplary endoscopic dilator in accordance with another as aspect of the present disclosure.

As shown in FIG. 5D, the dilator 500d can be shaped as a shell. FIG. 5D represents a dilator 500d having a shell-shaped outer surface including a convexly curved substantially continuous outer surface extending between the distal end 520 and the proximal end 522. Collectively, the dilator 500d may be formed from two portions hinge-connected through either a pin-hinge connection or a living hinge.

Figure 5E:
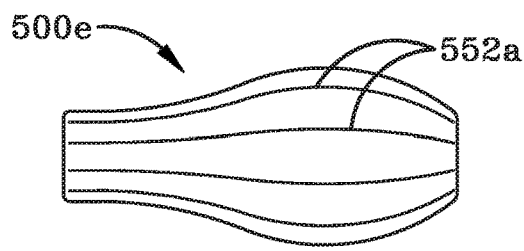
FIG. 5E is a diagrammatic side elevation view of a profile of another exemplary endoscopic dilator in accordance with another as aspect of the present disclosure.

FIG. 5E depicts a dilator 500e that is tapered with one or more external ridges 552a. Dilator 500e that may have a generally curved conical outer surface with a distal conical surface tapering towards an apex and further including a plurality of ridges 552a that similarly taper in a conical manner between the distal and proximal ends.

Figure 5F:
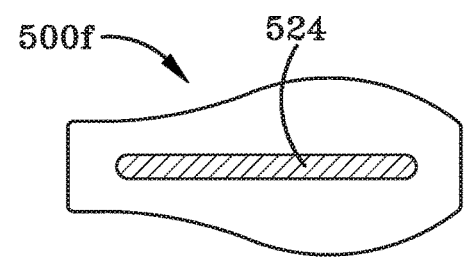
FIG. 5F is a diagrammatic side elevation view of a profile of another exemplary endoscopic dilator in accordance with another as aspect of the present disclosure.

As shown in FIG. 5F, the dilator 500f can include an elongated opening therein (i.e., that is open to the underlying scope). FIG. 5F further depicts dilator 500f that may be generally shell-shaped that is hingedly connected to define an aperture or opening 524 extending radially through the sidewall of the dilator 500f. The aperture 524 extending radially through the sidewall of the dilator 500f may be used to attach secondary components to the dilator 500f. Some exemplary secondary components may be additional plates, shields, covers, or shrouds that would effectuate an increase in the diameter of the dilator 500f when attached thereto. The aperture 524 may receive these additional components through a releasable connection and secure the same to the external surface of the dilator 500f. In this instance, dilator 500f may be used with secondary components to selectively increase the diameter of the dilator 500f from its base or standard diameter. Thus, dilator 500f may be considered a variable diameter dilator since it may be combined with secondary components to increase its overall outer diameter.

Figure 5G:
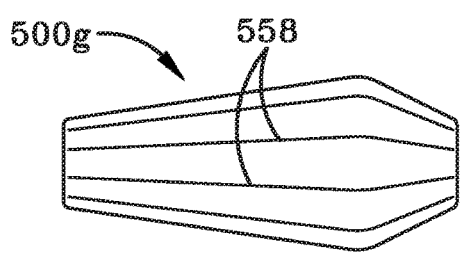
FIG. 5G is a diagrammatic side elevation view of a profile of another exemplary endoscopic dilator in accordance with another as aspect of the present disclosure.

FIG. 5G depicts dilator 500g with a conical taper between the proximal and distal ends having a plurality of ridges extending longitudinally along the outer surface thereof. In one particular embodiment, the ridges 558 taper complementary to the tapering distal section and the tapering proximal section. As such, the ridges 558 may culminate in an apex corresponding to an apex region where the tapered distal section meets the tapered conical section.

Figure 5H:
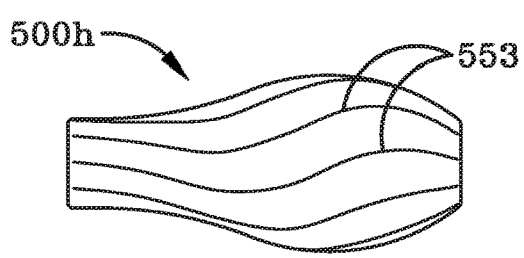
FIG. 5H is a diagrammatic side elevation view of a profile of another exemplary endoscopic dilator in accordance with another as aspect of the present disclosure.

FIG. 5H depicts a dilator 500h having spiraled ridges 553. Ridges 553 extend swirled or helically around an exterior surface. In some instances, there may be a plurality of ridges that swirl in a sinusoidal pattern circumferentially around the exterior surface of the dilator 500h. The overall profile of dilator 500h may have an elongated distal taper and a shortened proximal taper.

Figure 5I:
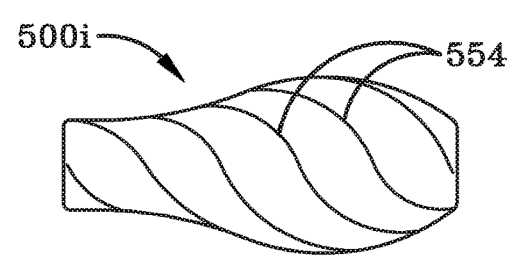
FIG. 5I is a diagrammatic side elevation view of a profile of another exemplary endoscopic dilator in accordance with another as aspect of the present disclosure.

As shown in FIG. 5I, the dilator 500i can include a cork-screw ridge 554 therein. FIG. 5I depicts a dilator 500i having circumferentially wound ridges that define a cork-screw configuration of the outer surface of the dilator 500i. The corkscrew ridges 554 extend longitudinally along the length of the dilator 500i from the distal end towards the proximal end while simultaneously winding circumferentially around the exterior surface thereof.

Figure 5J:
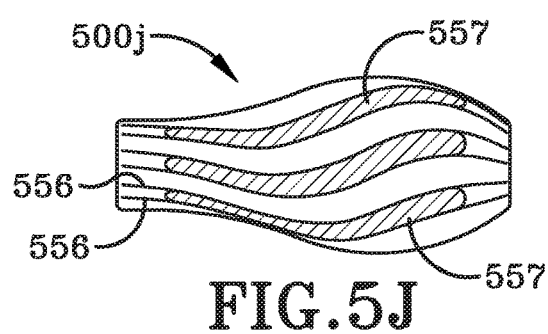
FIG. 5J is a diagrammatic side elevation view of a profile of another exemplary endoscopic dilator in accordance with another as aspect of the present disclosure.

As shown in FIG. 5J, the dilator 500j can include swirled ridges 556 separated by open spaces 557. FIG. 5J depicts a dilator 500j including swirled sections 556 defining therebetween swirled openings 557 extending longitudinally along the length of dilator 500j from the distal end towards the proximal end. Similar to the embodiment of dilator 500f in FIG. 5F, the openings 557 may be utilized to attach secondary or complimentary components to expand the diameter of the dilator 500j.

Figure 6A:
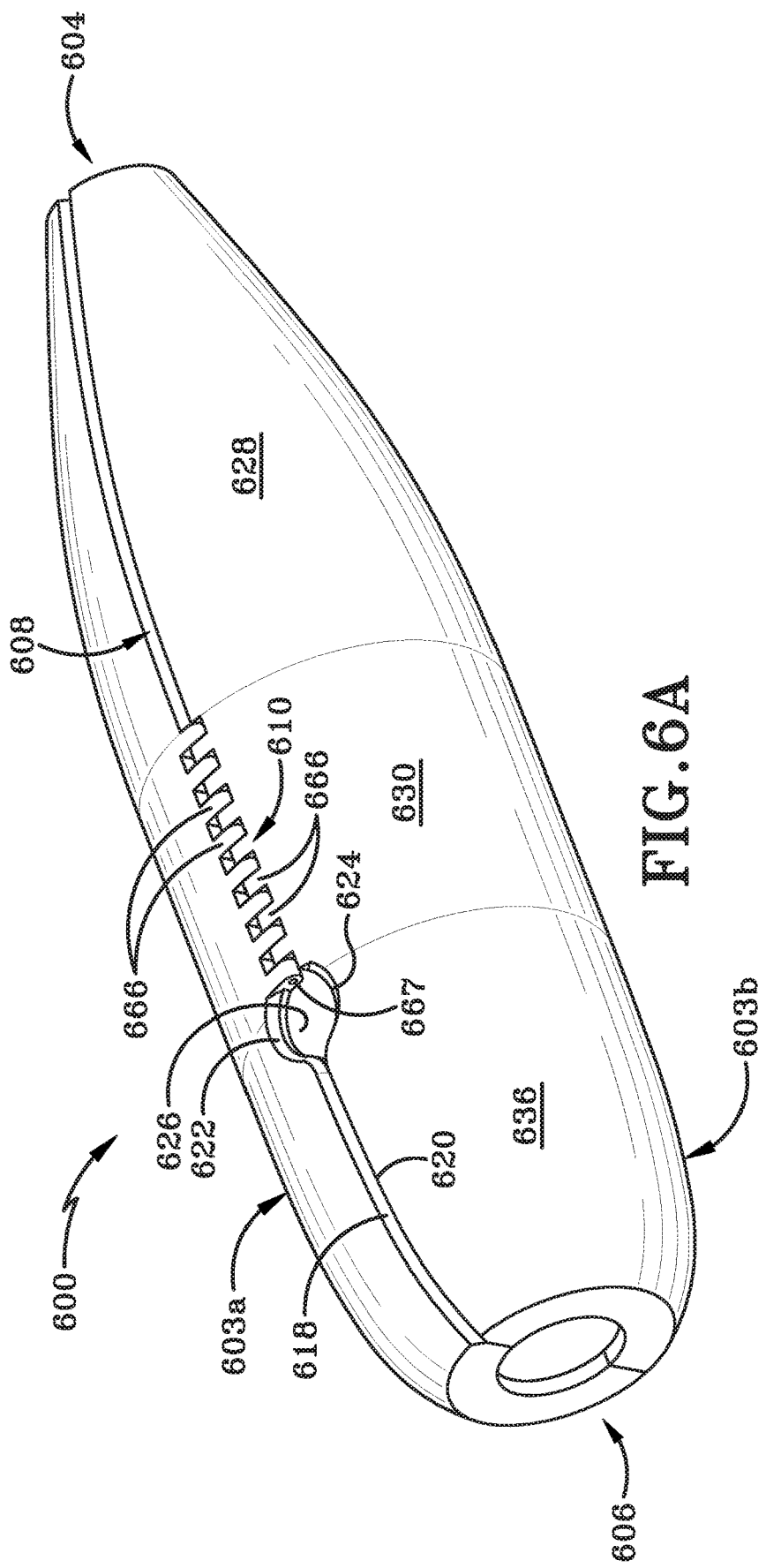
FIG. 6A is a perspective view of another endoscopic dilator formed from two parts hinged together in a closed position.
Figure 6B:
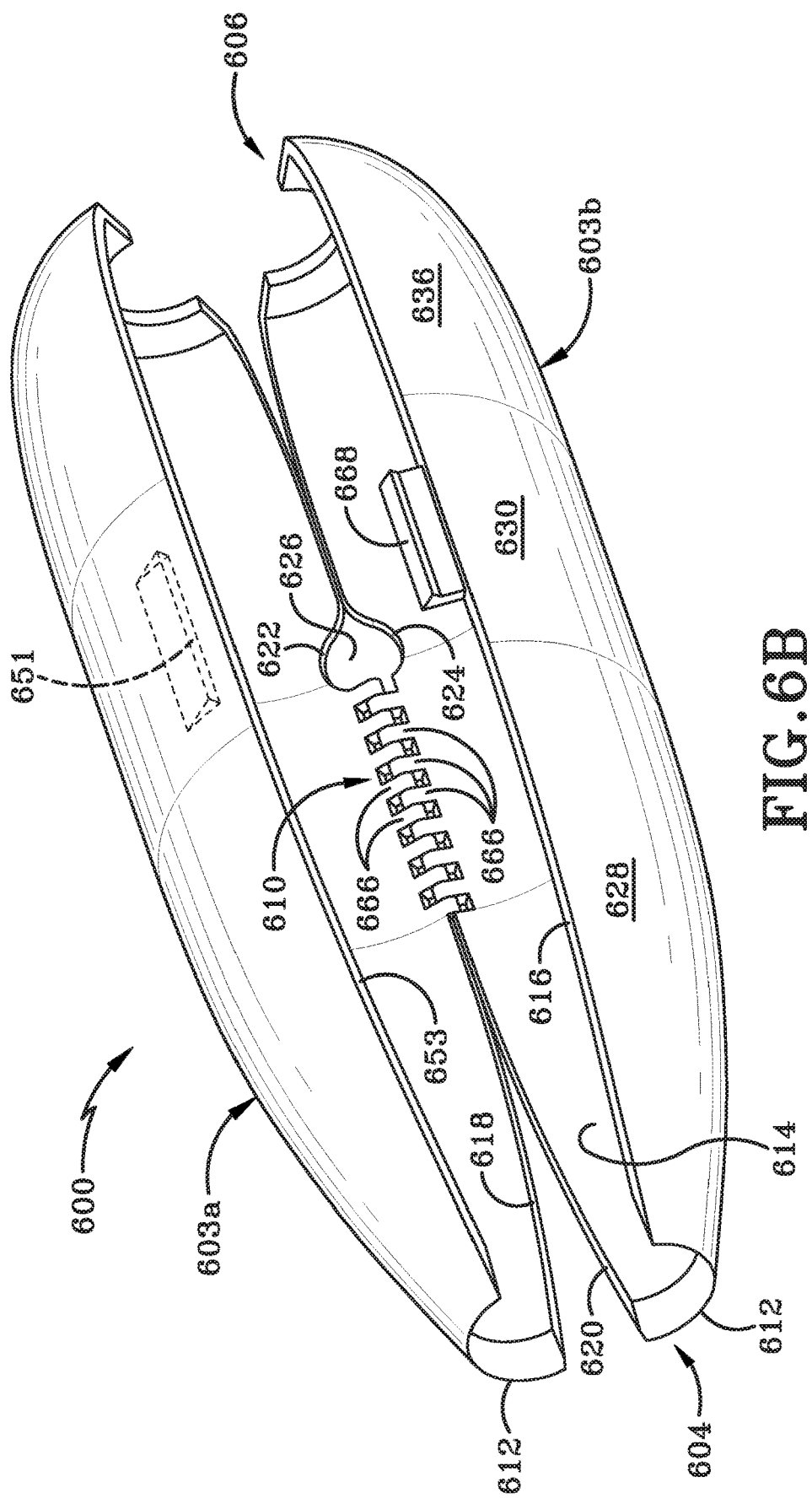
FIG. 6B is a perspective view of the endoscopic dilator of FIG. 6A formed from two parts hinged together in an open position.

Referring to FIGS. 6A-6C, the one or more parts 603a, 603b (i.e., first side segment 603a and second side segment 603b) of a dilator 600 as described herein can be attached and separated by a variety of mechanisms. For example, as shown in FIG. 6A, the two parts 603a, 603b can include offset and interlocking protrusions 666 thereon. A pin 667 can connect the two parts 603a, 603b on one side while a tight clamp 668 can connect the two parts 603a, 603b on the other side (note that FIG. 6C shows the dilator 600 separated at the clamp 668 for illustration only). To release the dilator 600 from a scope, the pin 667 can be pulled out.

With continued referenced to FIG. 6A, the distal end 604 of dilator 600 is spaced apart opposite the proximal end 606. A union 608 extends longitudinally along the length of the dilator 600 where the parts 603a, 603b join. First part 603a may generally be referred to as a first segment and the second part 603*b* may generally be referred to as a second segment. The interlocking teeth 666 define a hinge 610 about which the respective first side and the second sides of the hinge 610 are coupled together to pivotably connect the first segment or first part 603*a* and the second segment or second part 603*b* together. As shown in FIG. 6B, the first segment and the second segment or parts 603*a*, 603*b* pivot about the hinge 610 between an open position (FIG. 6B) and a closed position (FIG. 6A), wherein hinge 610 is defined by the interlocking protrusions 666 and pin 667. When the dilator 600 is in the open position (FIG. 6B), a portion of the endoscope is movable into engagement with the first segment or first part 603*a*, and/or the second segment or second part 603*b*.

A portion of an edge 618 on the first part 603*a* and a corresponding portion of an edge 620 on the second part 603*b* is interrupted by an arcuate edge 622 on the first part 603*a* and an arcuate edge 624 on the second part 603*b*. The arcuate edges 622, 624 are opposite each other and positioned proximately from the hinge 610. A space or aperture 626 is defined and bound by the arcuate edges 622, 624 and is in open communication with the interior cavity 614 of the dilator 600. The aperture 626 is sized to enable an operator to remove or insert the pin through corresponding apertures in the interlocking protrusion 666 in order to define the hinge 610. Thus, accordingly to one aspect of an exemplary embodiment, dilator 600 is configured to be disassembled as shown in the exploded perspective view of FIG. 6C by removing the pin 667 and enabling its install and disassembly through the aperture 626 defined by the arcuate edges 622, 624.

As depicted in FIG. 6B, the distal end 604 defines a semi-circular edge 612 that collectively define a distal opening when the dilator 600 is in the closed position. The distal opening is in open communication with an internal cavity 614 sized to receive the exterior surface of the tubular portion or cylindrical portion of the endoscope therein. A longitudinal edge 616 of the second segment or second part 603*b* includes a portion of connectors 668 that extends outwardly from edge 616 to removably or releasably connect the second part 603*b* to the first part 603*a*, via a complementary connector 651 formed near longitudinal edge 653 opposite the hinge 610. Accordingly, the first part 603*a* or first segment 603*a* is formed with a complimentary connector or component that receives connectors 668 in order to releasably secure dilator 600 in the closed position.

Dilator 600 includes a frustoconical first outer surface on the distal portion 628 that extends from the distal terminal end 604 and an apex region 630. Dilator 600 further includes a frustoconical second outer surface near the proximal portion that extends between the proximal terminal end 606 and the apex region 630. The first distal conical section 628 is longer than the frustoconical second section 636. As will be described in greater detail below, the distal section is configured to be advanced through the lumen of a body organ or structure or other bodily tissue before advancing the proximal portion or frustoconical second surface 636. In one particular embodiment, at least a portion of the first surface 628 is curved along the distal portion of the outer surface that extends between the terminal first distal end 604 and the apex region 630. Additionally, at least a portion of the second surface 636 is curved between the proximal end 606 and the apex region 630. In some embodiments, the curved first surface is concavely curved and in other particular embodiments the curved first surface may be convexly curved. Similarly, the proximal second surface 636 may be convexly curved or concavely curved. However, in the particular embodiment shown in FIG. 6A, dilator 600 includes a convexly curved first surface and convexly curved second surface 636.

As stated previously, the connector 668 on the second part 603*b* has a mating connector 651 on the first part 603*a* opposite the hinge 610. The connectors 651, 668, effectuate the releasable connection between the first part or first segment 603*a* and the second part or second segment 603*b*, and when the dilator is in the open position (FIG. 6B), the first connector and the second connector are disconnected and when the dilator is in the closed position (FIG. 6A), the first connector and the second connector 651, 668 are connected together.

Figure 7A:
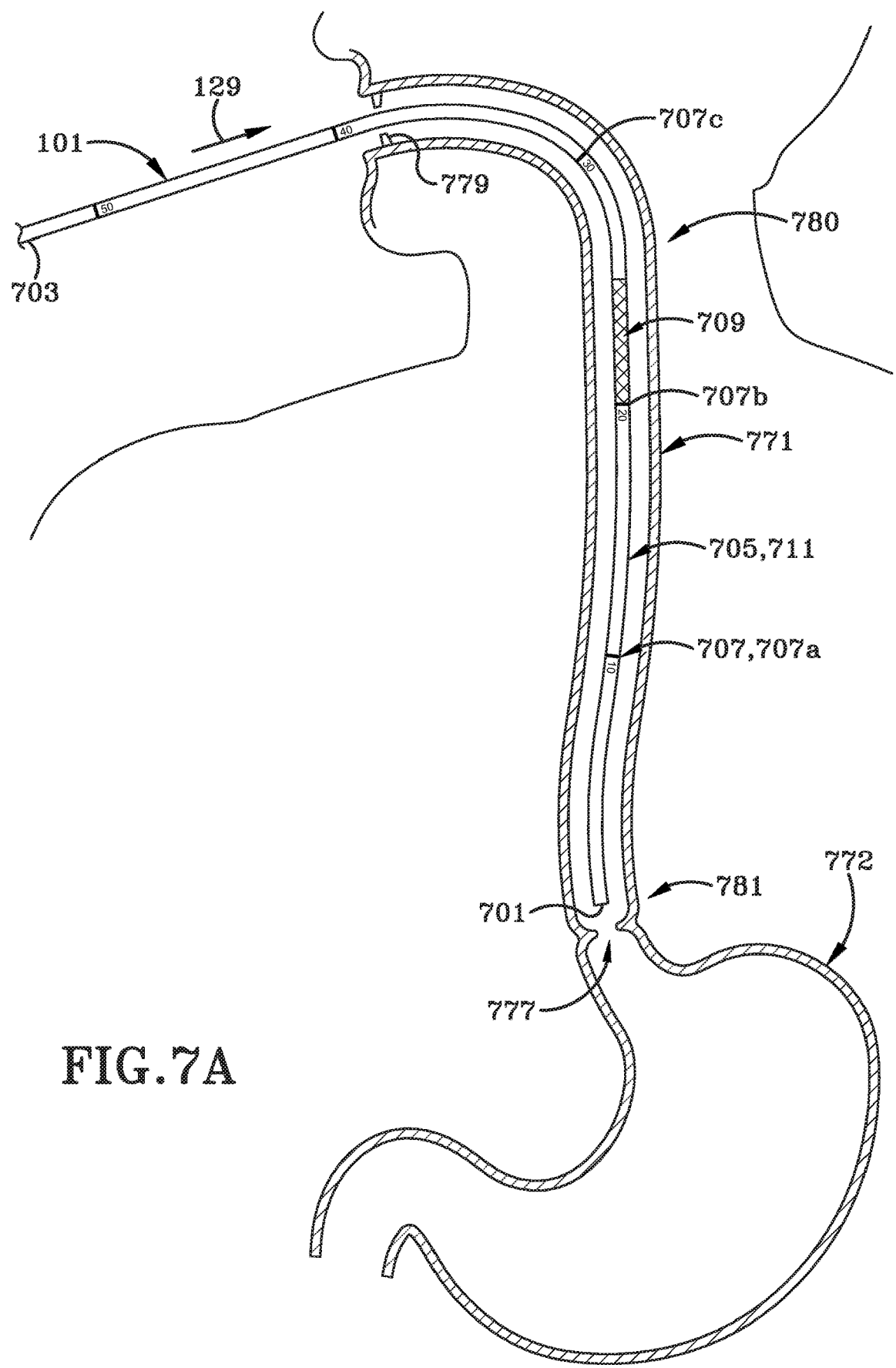
FIG. 7A is a diagrammatic operational view of an intubated esophagus with an endoscope inspecting a stricture located in the distal esophagus above the stomach.
Figure 7B:
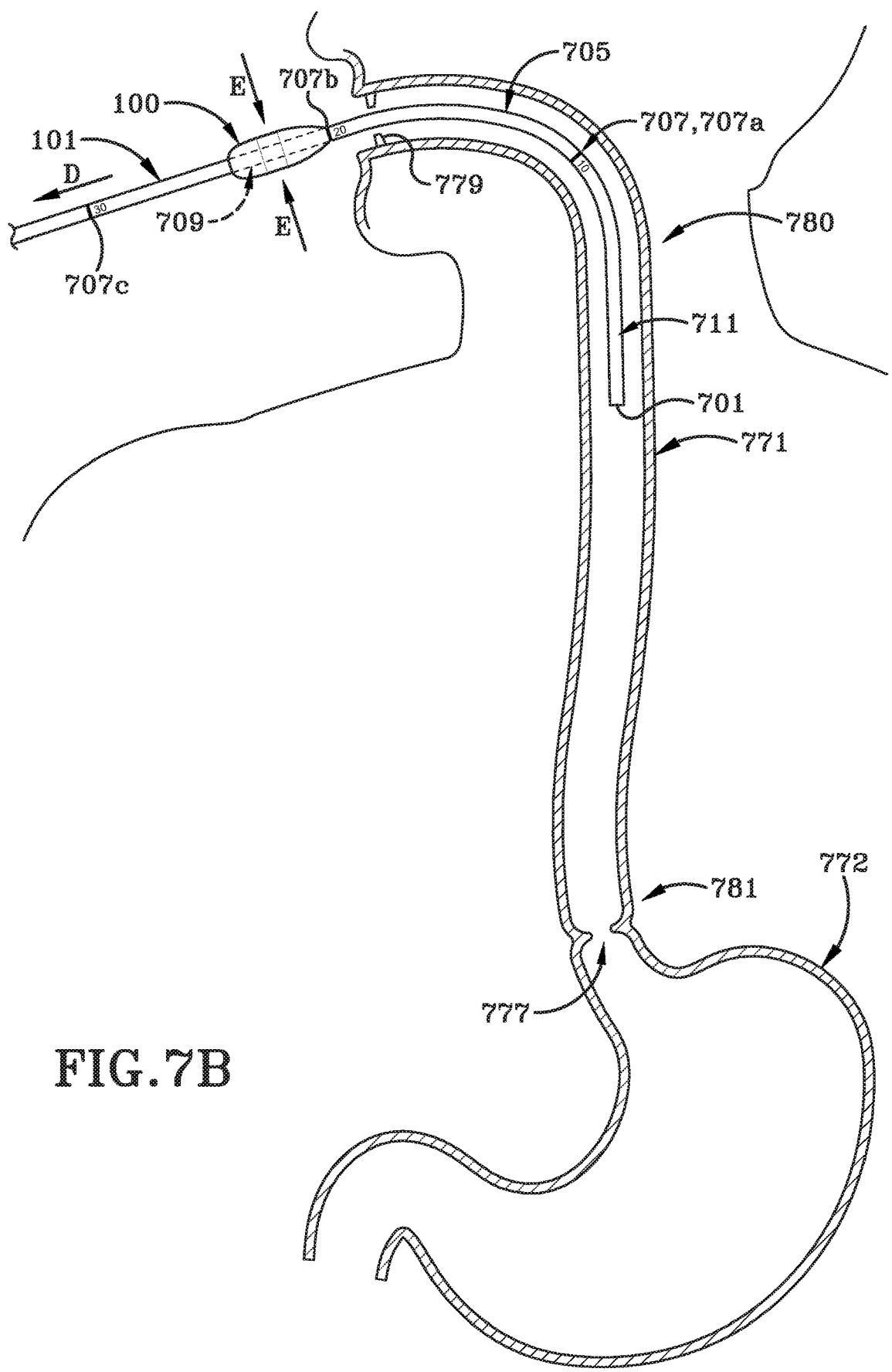
FIG. 7B is a diagrammatic operational view of the endoscope being extracted after having inspected the stricture, per FIG. 7A, and connected an exemplary dilator to the body of the endoscope while a distal end of the endoscope remains intubated within the esophagus.
Figure 7C:
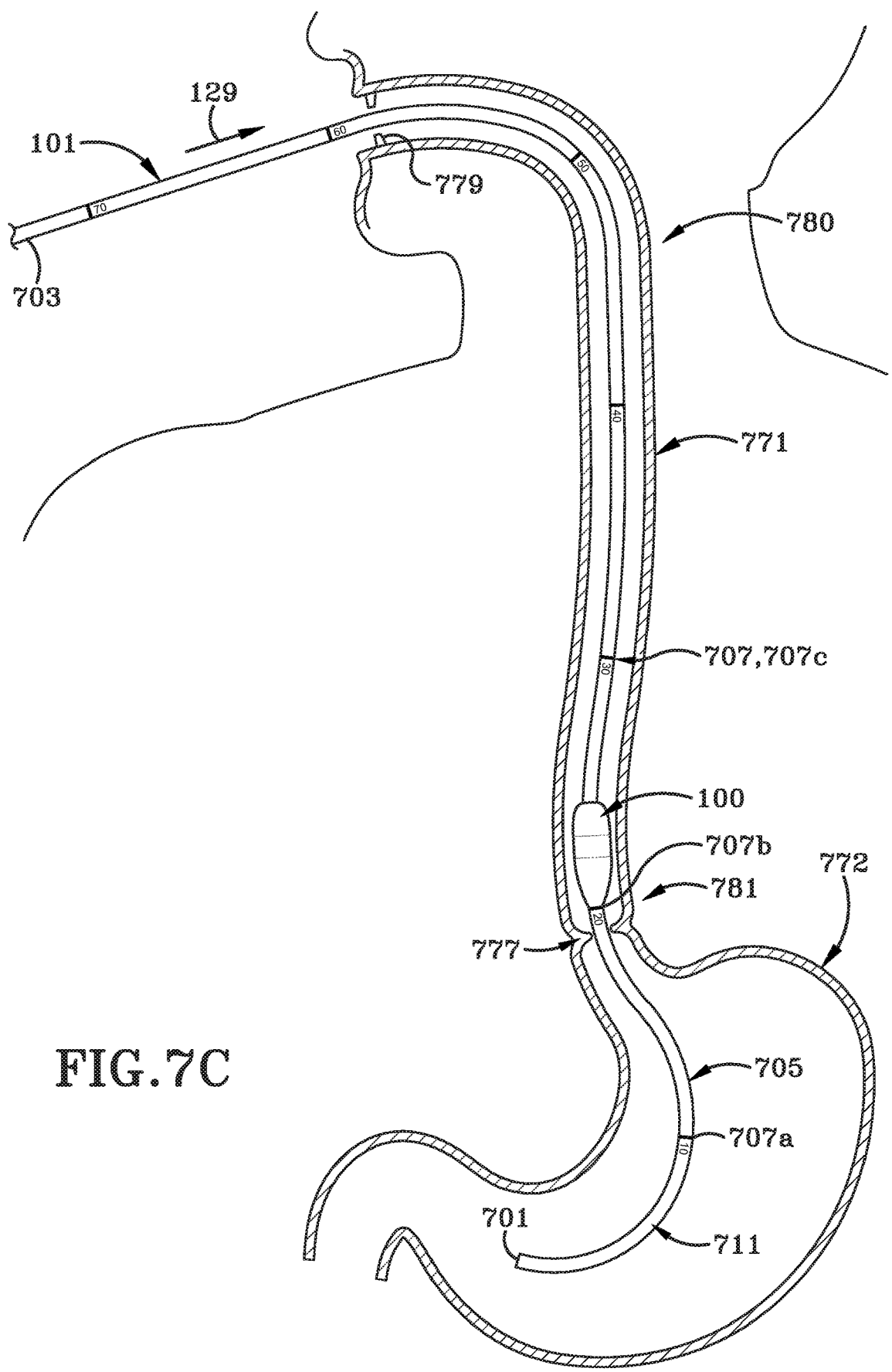
FIG. 7C is a diagrammatic operational view of the distal end of the endoscope advancing past the stricture and the dilator approaching the stricture.
Figure 7D:
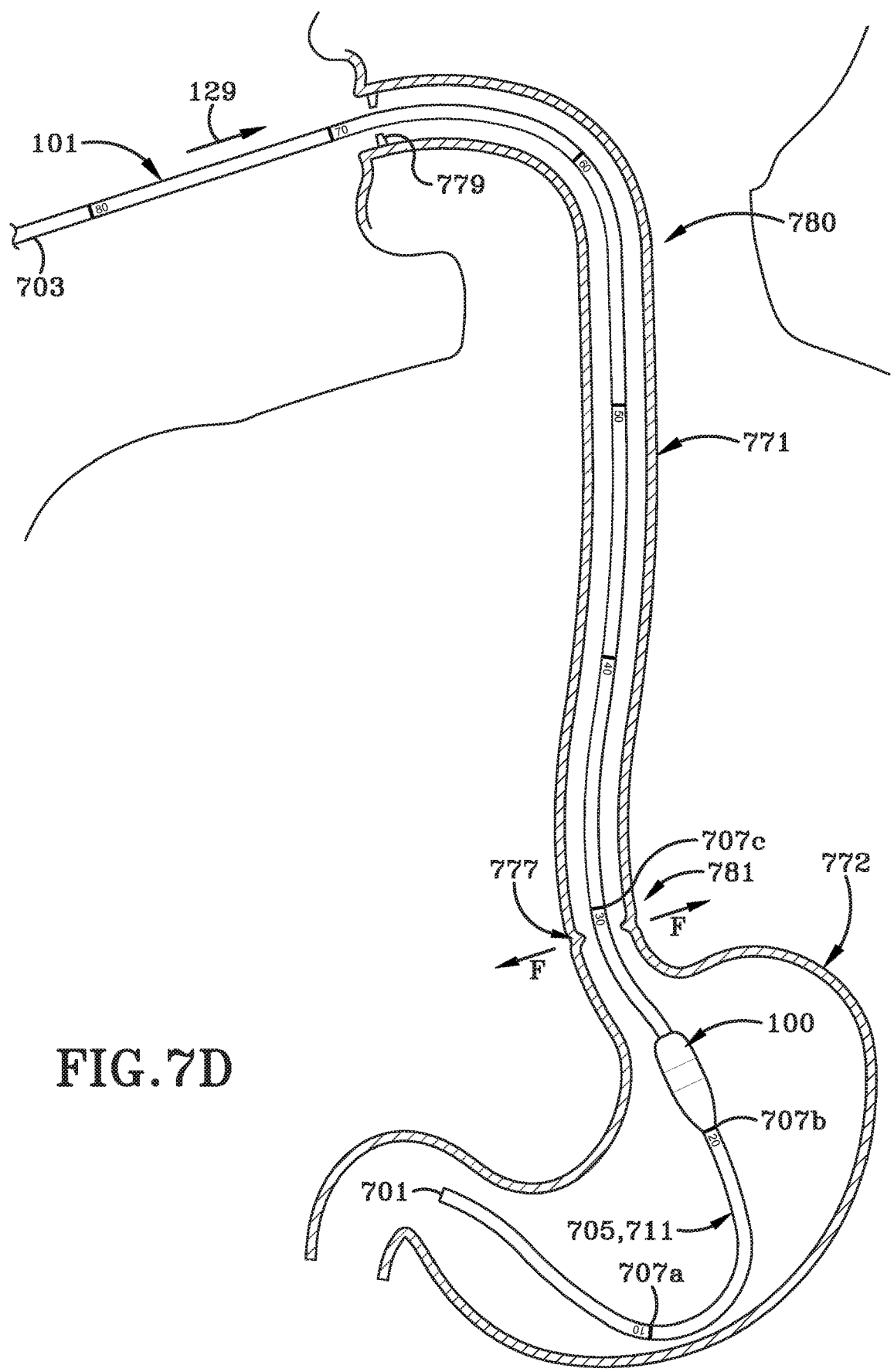
FIG. 7D is a diagrammatic operational view of the distal end of the endoscope advancing further into the stomach and the dilator having been moved through the stricture and the stricture in a dilated state.
Figure 9:
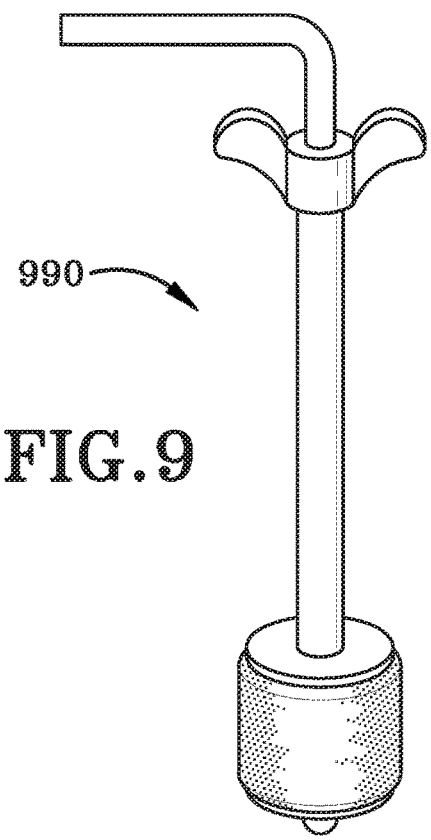
FIG. 9 shows an expansion mechanism for a variable diameter endoscopic dilator.

Referring generally to FIGS. 7A-7D, in use to dilate the esophagus, the endoscope 101 can first be inserted into the esophagus 771 to evaluate the stricture 777. The endoscope 101 can be, for example, 100 cm or more in length. The esophagus 771 generally starts at a position 780 that is about 15-17 cm from the incisors 779 and ends at a position 781 that is at about 38-40 cm from incisors 779. Then the stomach 772, when it is distended, measures over 35 cm. Most strictures (more than 95%) are around 38-40 cm from the incisors. As shown in FIGS. 7A and 7B, the endoscope 101 can be pushed down to the stricture 777, which is about 40 cm from the incisors. The stricture 777 can be evaluated with the scope 101. Referring to FIG. 7B, the scope 101 can be withdrawn back to the 20 cm mark (i.e., 20 cm from the distal end of the esophagus 781). That means the tip of the scope 101 is still in the esophagus 771. The dilator can be attached between 20-25 cm. As shown in FIG. 7C, the scope 101, with attached dilator 100, is moved down again to the stricture 777 where the scope 101, with the attached dilator, is pushed through the stricture 777 into the stomach (as shown in FIG. 7D). Because the stomach is much longer than 20 cm, the distal end of the scope (last 20-25 cm) easily fits into the stomach cavity. After dilation, the scope 101 and the dilator can be easily partially withdrawn such that the dilated stricture can be viewed through the scope 101. If there is a need for additional (sequential dilation), the endoscope 101 can be withdrawn until the dilator is again out of the oral cavity, a dilator similar to dilator 100 but with a wider diameter can replace the dilator 100, and the process can be repeated. Notably, any of the dilators described herein before or after can be utilized in accordance with the operational method discussed with reference to FIG. 7A-FIG. 7D.

FIG. 7A depicts that a typical endoscope 101 includes a distal end 701 and a proximal end 703 depicted schematically or diagrammatically as a break line. Scope 101 includes a substantially tubular or cylindrical body including an exterior surface 705 extending between the distal end 701 and the proximal end 703. In one particular embodiment, the exterior surface of the body 705 of the endoscope 101 may include delineations or markings 707 identifying a dimensional distance of the endoscope 101 relative to the distal end 701. For example, a first marking 707*a* may be 10 centimeters, or 1 decimeter, or 100 millimeters from the distal end 701. A second marking 707*b* may be 20 centimeters, or 2 decimeters, or 200 millimeters from the distal end 701 and spaced at an equal interval from the first marking 707*a*. The marking intervals continue in regular patterns or regular intervals towards the proximal end 703. As will be described in greater detail below, the markings exterior to the tubular body 705 of the endoscope 101 are useful inasmuch as the dilators disclosed herein are configured to be attached to the endoscope 101, via the tubular body 705 at a location that is in between the second marking 707*b* and the third marking 707c which corresponds to a distance in a range from about 20 centimeters to about 30 centimeters. The attachment location 709 may be in a range from about 20 centimeters to about 25 centimeters from the distal end 701. As will be described in greater detail below, the reason for the attachment location 709 is that the dilator may be connected to the tubular body 705 of the endoscope 101 while the distal portion of the endoscope tubular body 705 relative to the attachment location 709 remains intubated within the esophagus 771 while connecting the dilator thereto. By enabling the distal portion 711 to remain intubated and extending beyond the starting position 780 of esophagus 771, this prevents the need for intubating the patient twice which can be difficult or otherwise potentially damaging or otherwise disruptive.

FIG. 7B depicts an operational use of an exemplary dilator of the present disclosure being connected to the endoscope tubular body. FIG. 7B further depicts that the dilator is attached to the endoscopic tubular body 705 after having inserted a portion of the endoscope into the esophagus 771 then, the distal end 701 of the tubular body 705 is passed into the esophagus 771 towards the stomach 772. Further, the distal end having already been approached towards the stricture 777 that is positioned between the lower end of the esophagus 771 and the stomach 772. The endoscope allows the surgeon or the gastroenterologist or other medical personnel to inspect the stricture 777 and approximate the diameter thereof. Returning to FIG. 7B, endoscope is depicted as being extracted, or at least a portion of the endoscope is extracted in the direction of arrow D while leaving the distal end 711 intubated within the esophagus 771 distally relative to the beginning 780 or start 780 of the esophagus. FIG. 7B further depicts connecting the dilator to the tubular body 705 of the endoscope 101 as indicated by arrows E. The dilator is connected in the attachment region 709 which is located proximally from the second marking 707b and may be, in one particular embodiment, in a range from about 20 centimeters to about 30 centimeters to the distal end 701 of the tubular body 705.

As shown with various embodiments used herein, any of the dilators described herein may be operable with the method of operation depicted in FIGS. 7A through 7D. Accordingly, connecting the dilator to the extracted portion of the endoscope may include contacting ridges formed at a distal end of the dilator with an exterior surface of the extracted portion of the dilator. The ridges in this scenario would be formed along the inner surface of one part of the dilator such that the dilator substantially circumscribes the exterior surface of the extracted portion of the tubular body 705 of the endoscope 101. Further, connecting the dilator to the extracted portion of the endoscope may include releasably securing the first part to a second part of the dilator via a snap fit connection as identified in some of the embodiments depicted in FIG. 1 through FIG. 6 (or any of the embodiments described below in FIG. 8 through FIG. 19). Accordingly, corresponding and mating connectors may complement each other on respective parts that are offset opposite to the hinge enabling the dilator to releasably move between open and closed positions. Towards this end, the matable connectors are often located approximately 180 degrees from the hinge connecting the first part to a second part relative to a pivot in order to pivot about a pivot axis. When the dilator includes a rectangular recess, a first high friction component formed from a polymer or monomer material may be aligned adjacent or on the inner surface of one of the parts forming the dilator. Similarly, a second high friction component may be aligned adjacent or on an inner surface of a second part of the dilator such that when the dilator is moved to the closed position, the two high friction components formed from polymeric or monomeric materials frictionally engage through an interference fit the exterior surface of the tubular body 705 of the endoscope 101. Thus, the mating connectors enable a sufficient amount of force to be imparted between the high friction components and the exterior surface of the body 705 so as to prevent the dilator from moving or translating along the longitudinal length of the endoscope 101. Further, when connecting the dilator to the extracted portion of the endoscope 101, the inner diameter of the dilator formed by the two parts hinged together and moving towards the closed position is minimized so as to minimize the internal diameter of the dilator measured between the complementary inner surfaces of the first part and second part. When the internal diameter is minimized in the closed position, the inner surfaces may be in direct contact with the exterior surface of the tubular body 705 of the endoscope 101.

FIG. 7C depicts an operational view of the embodiment in which the distal end 701 of the tubular body 705 has been advanced through the stricture 777 at the end 781 of the esophagus 771. The distal portion 711 is within the stomach 772 and the distance between the distal end 701 and the beginning of where the distal end of the dilator 100 sufficiently short so as to remain undisturbed within the stomach 772. The endoscope 101 continues to advance in the insertion direction as indicated by arrow 129.

FIG. 7D depicts that the endoscope 101 is inserted in the direction of arrow 129 to advance the dilator 100 through the stricture 777 in order to dilate and increase the diameter of the stricture as indicated by arrows F. After dilating the stricture 777, the endoscope 101 may be removed from the esophagus 771 by carrying and moving the dilator proximally through the stricture 777 having been dilated. It is possible that on the way out/during extraction, the stricture 777 may be inspected for a second time to confirm that it has been dilated properly by the dilator. Then, if the proper dilation of the stricture 777 is confirmed, the dilator and endoscope may be removed from the esophagus in a direction opposite that of arrow 129. In some exemplary embodiments, the process of identifying whether the stricture has been dilated to the preferred diameter may require additional steps if the stricture has not be dilated to the preferred diameter. For example, if upon inspection, for the second time, of the stricture 777, the surgeon or gastroenterologist determines that the dilator did not dilate the stricture to a preferred diameter, then the dilator may be removed and a portion of the endoscope, where the attachment region 709 is located, may be pulled outwardly from the patient's mouth while leaving the distal end 711 of the body 705 intubated within the esophagus. Then, using an adjustable diameter dilator, the surgeon or gastroenterologist may adjust an external diameter of the dilator while the dilator is outside of the esophagus. Thereafter, then moving the dilator after having its external diameter adjusted through the stricture for the second time. In some implementations, as will be identified below, adjusting the external diameter may be accomplished by attaching a cover or shroud to an outer surface of a first part of a dilator or attaching a second cover or second shroud to another portion of an outer surface on the second part of the dilator. Alternatively, the external diameter of the dilator may be adjusted by increasing the external diameter by rotating a threaded or a free spinning component on the dilator. In some instances, the rotation of one component of the dilator causes another portion of an outer surface to translate along an axis to flare or otherwise increase the outer surface or exterior diameter of the dilator.

As shown in FIGS. 8A and 8B, in some embodiments, an expandable dilator 800 can include a rotatable knob 824 having an indicator 807 thereon that, when rotated, indicates the diameter of expansion. For example, FIG. 8A and FIG. 8B depict an exemplary dilator 800 that may increase its diameter from 51 French to 54 French upon rotation of a proximal portion 803 that may rotate about a longitudinal axis relative to a distal portion 805.

FIG. 8A and FIG. 8B further depict that the dilator 800 may be formed of two parts, namely a first part 803 and a second part 805. The first part may be referred to as the proximal part 803 and the second part may be referred to as the distal part 805. Thus, while dilator 800 is formed from two parts, each part 803, 805 entirely circumscribes the tubular body of the endoscope 801. Thus, this embodiment may include two fully circumferential parts that are aligned tandemly end to end. Particularly, the first part 803 has an indicator 807 that aligns and corresponds to markings 809 on the second part 805. Thus, when the first part 803 freely rotates around the longitudinal axis as indicated by arrow G, the indicator 807 moves to another portion of the markings 809 as the first part 803 translates in the direction of arrow H which is parallel to the insertion direction 129 to increase the external diameter of dilator 800 as indicated by arrow I.

The adjustable diameter dilators 200, 300, 800 can be used to dilate a stricture similar to that as described above with respect to dilator 100. However, the width of the diameter can be increased during use for repeat dilation with immediate re-inspection of the stricture (i.e., immediate pull-back and viewing with the scope).

Figure 11:
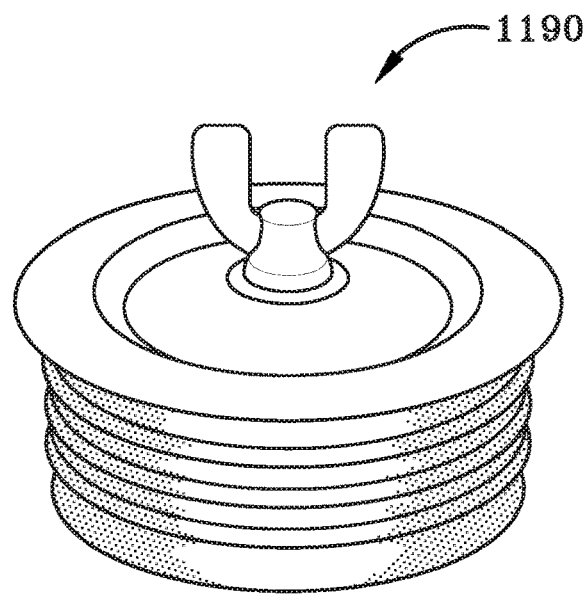
FIG. 11 shows another expansion mechanism for a variable diameter endoscopic dilator.
Figure 10A:
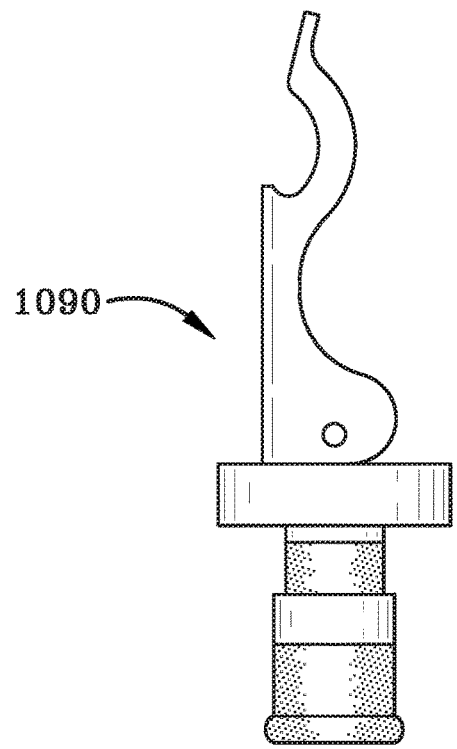
FIG. 10A depicts another expansion mechanism for a variable diameter endoscopic dilator in a first or neutral position.
Figure 10B:
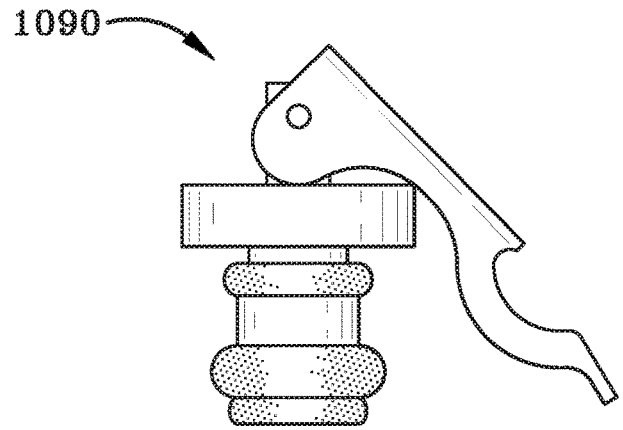
FIG. 10B depicts the expansion mechanism for the variable diameter endoscopic dilator of FIG. 10A in a second or expanded position.

Although a screw and wedge mechanism is described for expanding the diameter of dilators 200, 300, 800, other mechanisms are possible. For example, a balloon can be placed within the lumen of the dilator that can be inflated with water or air using a syringe or other type of inflating device. Other mechanisms for expansion of a dilator include, but are not limited to: an expansion mechanism 990 that is similar to a pipe expansion plug (see FIG. 9), an expansion mechanism 1090 that is similar to a bottle stopper seal cork (FIGS. 10A and 10B), or an expansion mechanism 1190 that is similar to a wingnut plug (FIG. 11).

FIG. 12A depicts a single dilator 1200 that can include several different sections 1212a, 1212b, and 1212c of differing diameter (e.g., increasing from the distal end 1205 to the proximal end 1207). In one embodiment, the largest diameter of the distal-most section 1212a can be 51 French, the largest diameter of the middle section 1212b can be 54 French, and the largest diameter of the proximal-most section can be 57 French. The sections 1212a, 1212b, and 1212c can each have a shape and/or configuration as described above with respect to any of the other dilator embodiments. The sections 1212a, 1212b, 1212c may be formed from a unibody member.

FIG. 12B depicts a collective dilator 1200' multiple dilators arranged serially (i.e., in series) or tandemly end-to-end. Namely, first dilator 1212a', second dilator 1212b', third dilator 1212c' each having a different external diameter (e.g., increasing from the distal end 1205' to the proximal end 1207'). In one embodiment, the largest diameter of the distal-most dilator 1212a' can be 51 French, the largest diameter of the middle dilator 1212b' can be 54 French, and the largest diameter of the proximal-most dilator 1212c' can be 57 French. The dilators 1212a', 1212b', 1212c' can each have a shape and/or configuration as described above with respect to any of the other dilator embodiments.

Figure 13:
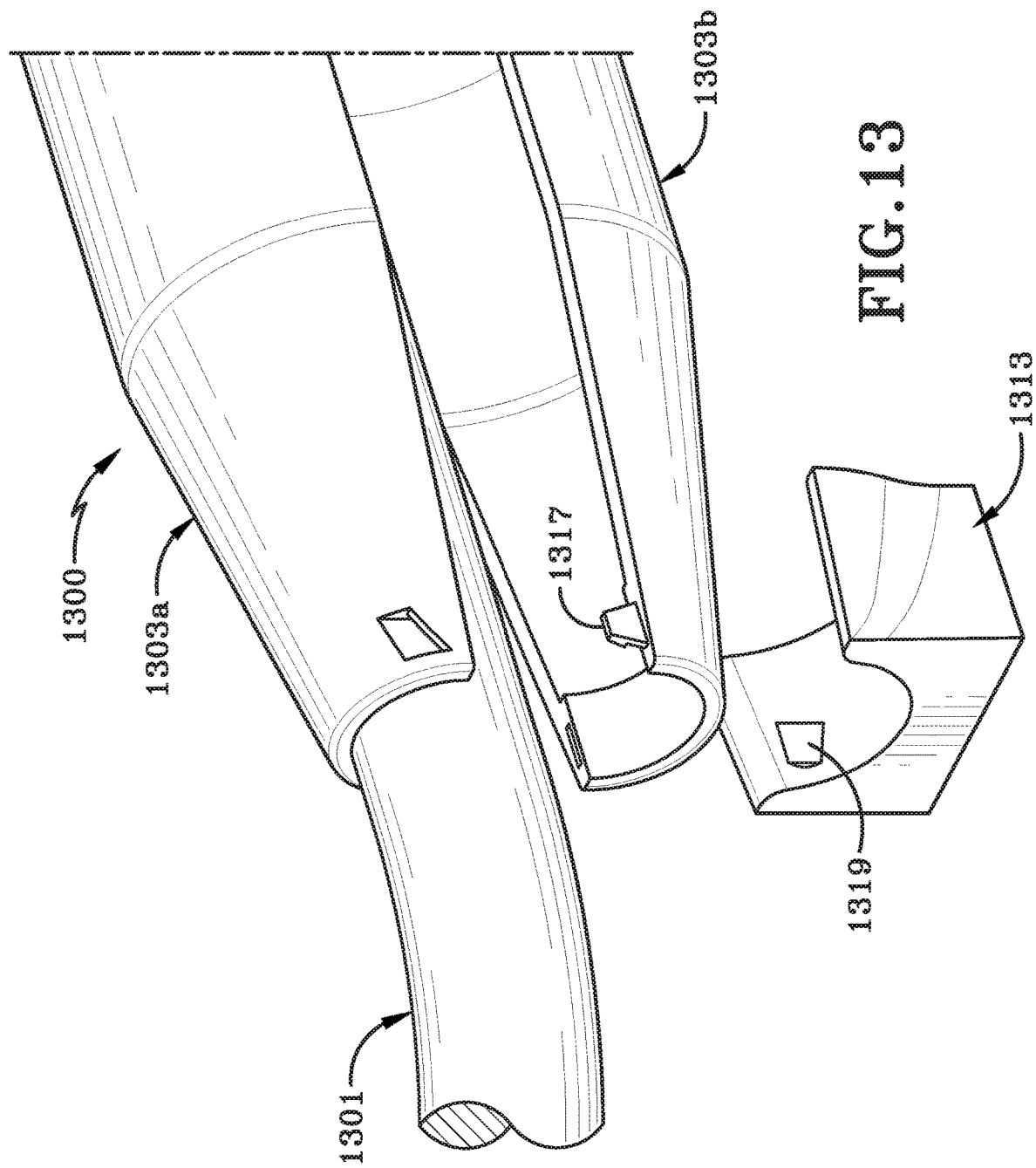
FIG. 13 depicts an exemplary tool to remove a dilator from a scope.

FIG. 13 depicts a tool 1313 for disassembly used to quickly remove the dilators described herein from the scope. Tool 1313 separates dilator 1300 from a scope 1301 into two parts 1303a, 1303b. The tool 1313 includes a table mount base that is configured to press one or more release buttons 1317 (e.g., with tab 1319). The tool 1313 can be configured to activate only one button 1313 at a time (and then be flipped) or can be configured to activate two or more buttons simultaneously.

Figure 14:
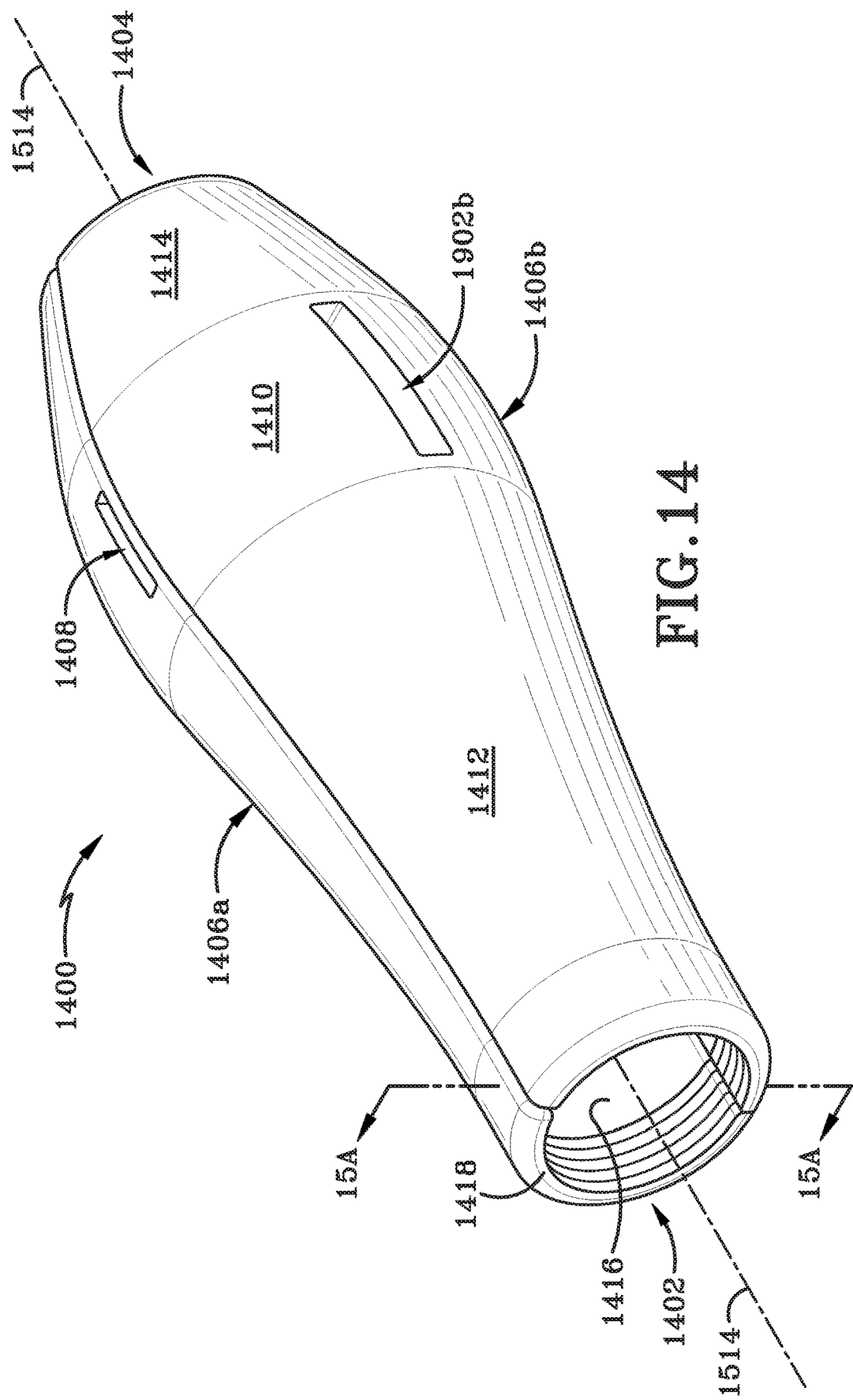
FIG. 14 is a perspective view of another exemplary endoscopic dilator.

FIG. 14 depicts an exemplary dilator 1400 having a distal end 1402 and a proximal end 1404 configured to removably connect with the exterior surface of the tubular body of an endoscope. Similar to other embodiments, dilator 1400 is formed of a first part 1406a and a second part 1406b (which may also be referred to as first side segment 1406a and second side segment 1406b) which each substantially circumscribe the cylindrical body of the endoscope approximately 180 degrees. The first part 1406a is formed with an aperture or slot 1408 extending longitudinally along the apex region 1410. Apex region 1410 defines the maximum external diameter of the dilator 1400 and may be convexly curved. Slot 1408 may be a rectangular slot having two parallel edges extending longitudinally and two short parallel edges that extend circumferentially around the exterior surface of the apex region 1410. In one particular embodiment, slot 1408 is a through aperture that extends entirely through the wall defining part 1406a so as to provide an open communication with the interior cavity of dilator 1400. As will be described in greater detail below, slot 1408 may be utilized to receive a release pin inserted therein to facilitate the disconnection of the releasable connectors extending between the first part and the second part 1406a, 1406b. Similar to the other embodiments depicted herein, dilator 1400 may include a distal section 1412 of the outer surface and a proximal section 1414 of the outer surface, where in the apex region 1410 is located intermediate the distal section 1412 and the proximal section 1414.

When the dilator 1400 is in the closed position (as shown in FIG. 14) the distal end 1402 defines an end aperture 1416 more particularly an inner surface of each respective part 1406a, 1406b defines the interior cavity in open communication with a terminal end wall 1418 circumscribing at least 180 degrees but at least partially define the end aperture 1416.

With continued reference to FIG. 14, dilator 1400 may additionally include a slotted aperture 1902b in the second part 1406b that connects supplemental or secondary components to the exterior surface of part 1406b. The description of slotted aperture 1902b is more fully referenced below with respect to FIG. 19A-FIG. 19C.

Figure 15A:
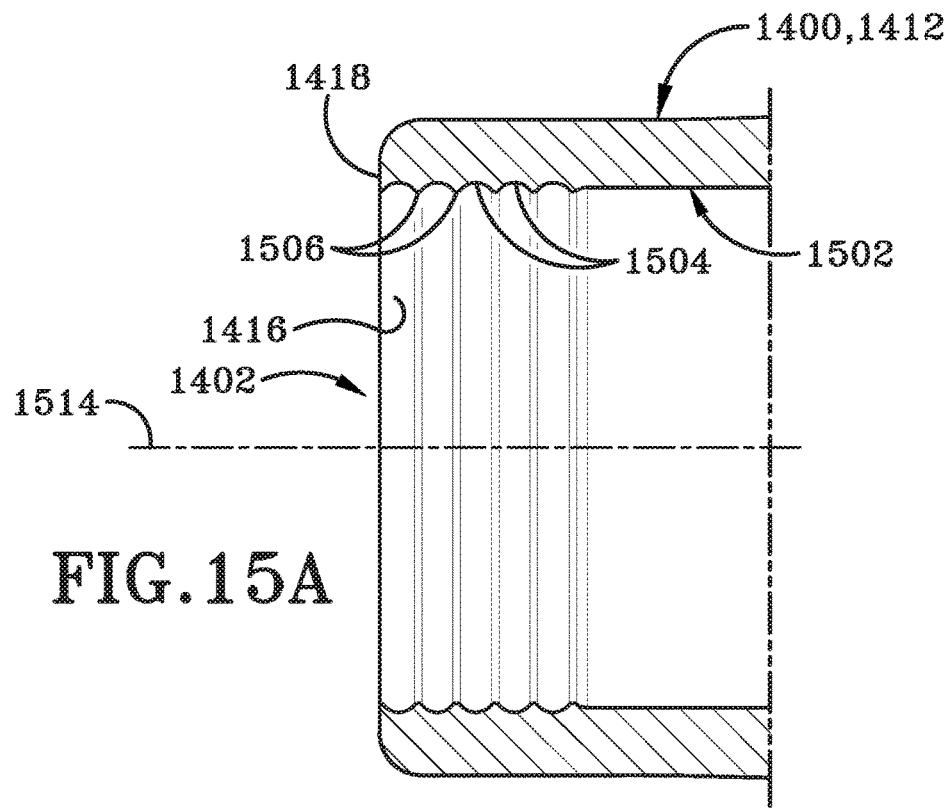
FIG. 15A is a cross section view taken along line 15A-15A in FIG. 14 depicting a configuration of an inner surface of the dilator.
Figure 15B:
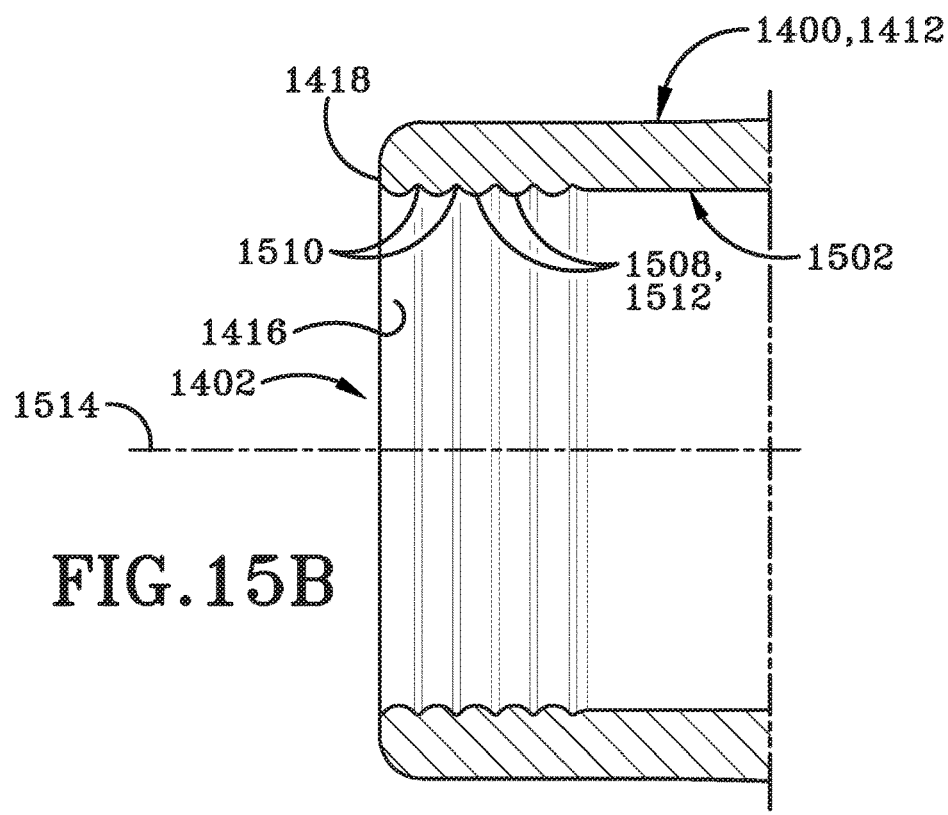
FIG. 15B is a cross section view similar to that of FIG. 15A depicting another configuration of the inner surface of the dilator.

FIG. 15A and FIG. 15B depict that the inner surface 1502 of the distal end 1402 of dilator 1400 may define ridges that are configured to interlock or frictionally engage the exterior surface of the body of the endoscope. FIG. 15A depicts that the ridges may include concavely curved edges 1504 so as to define points 1506 between adjacent concave edges 1504 that frictionally engage the exterior surface of the tubular body of the endoscope. FIG. 15B depicts the ridges as having convexly curved surfaces 1508 that define intermediate valleys 1510 and the convex ridges 1508 have an apex 1512 that is configured to frictionally engage the exterior surface of the endoscope. In one particular embodiment, the respective curved surfaces, regardless of whether concave surfaces 1504 or convex surfaces 1508 are aligned parallel and extend circumferentially around a longitudinal axis 1514. However, it is entirely possible that the concave or convex surfaces defining the ridges at the distal end 1402 of dilator 1400 may be angled relative to longitudinal axis 1514 so as to emulate or effectively operate as threads.

Figure 16A:
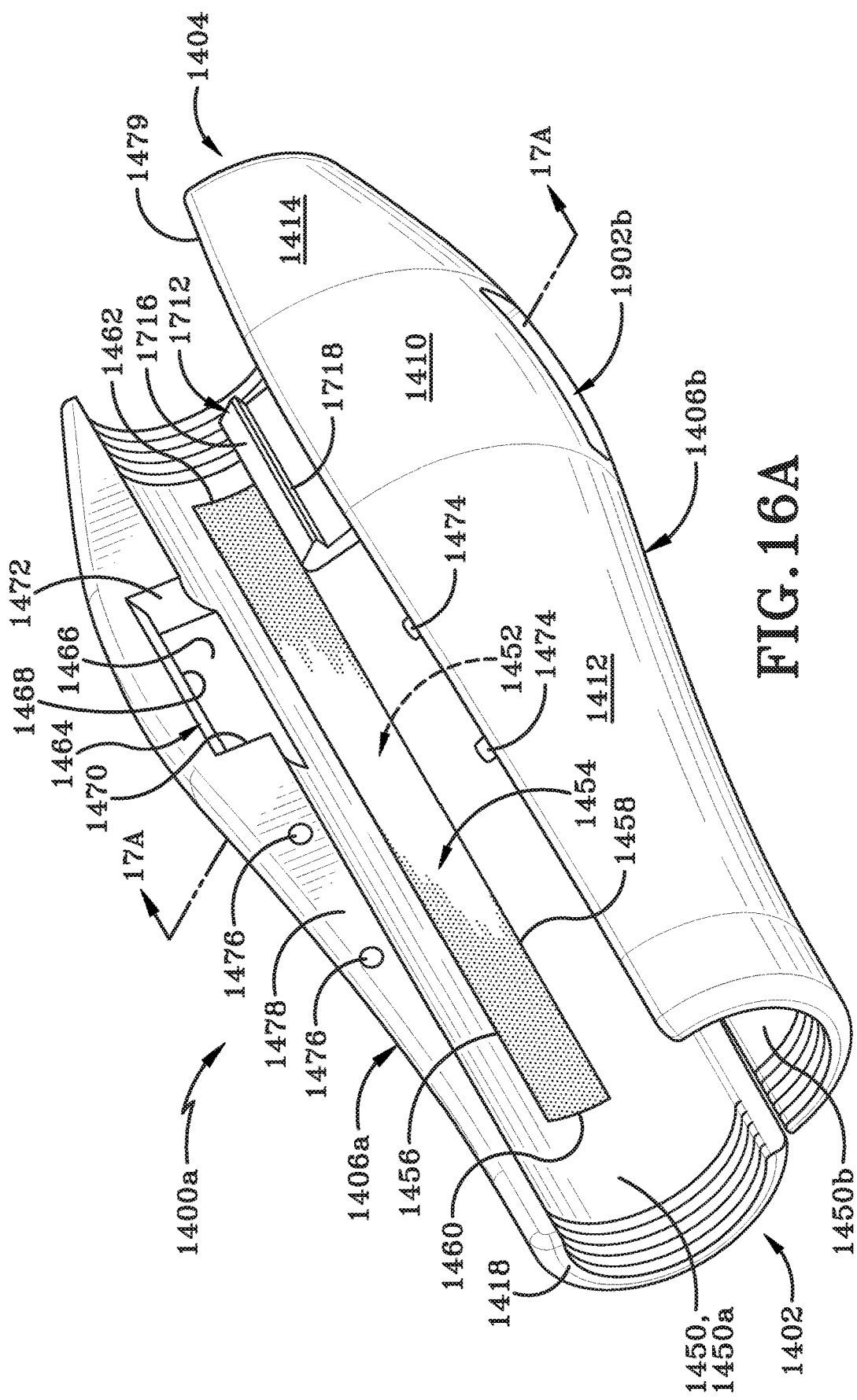
FIG. 16A is a perspective view of a dilator having a high friction component on the inner surface and the dilator shown in an open position.
Figure 16B:
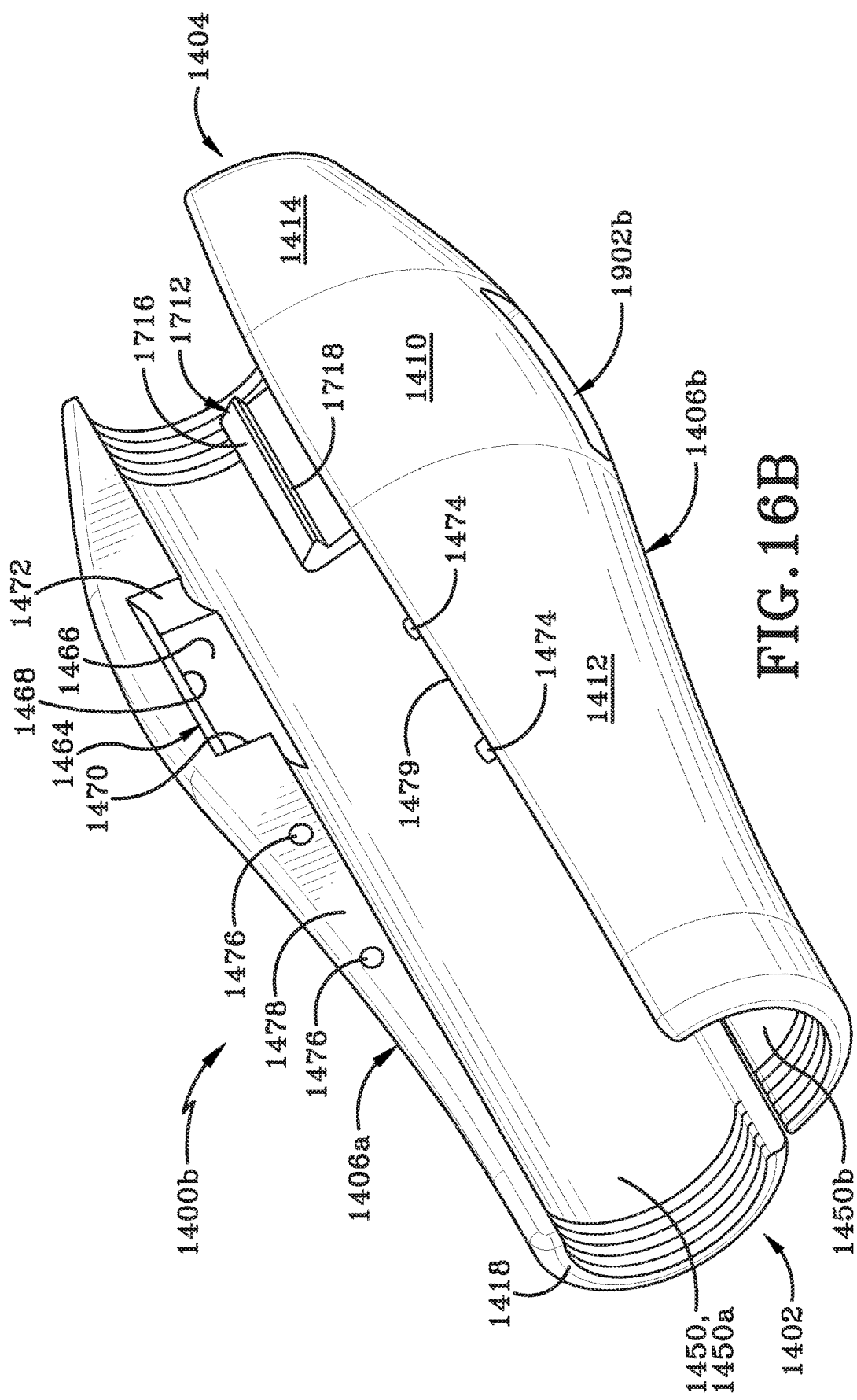
FIG. 16B is a perspective view of a dilator having a substantially continuous inner surface and the dilator shown in an open position.

FIG. 16A, FIG. 16B, and FIG. 16C depict various versions of dilator 1400 which are shown as dilator 1400a, dilator 1400b, and dilator 1400c, respectively. Each of the dilators 1400a, 1400b, and 1400c are shown in their open position to identify differing internal structures and configurations that enable the respective dilator to connect with the exterior surface of the tubular body of an endoscope.

FIG. 16A depicts dilator 1400a as having ridges formed in its distal end and ridges formed in its proximal end. As stated previously, the ridges assist with grasping the exterior surface of the body of the endoscope when the two parts are pivoted about a pivot axis 1701 (FIG. 17A) to the closed position, as shown in FIG. 17B. Dilator 1400a includes a concave semicircular elongated inner surface 1450. More particularly, concave inner surface 1450a is on the first part 1406a and concave inner surface 1450b is on the second part 1406b. Inner surface 1450 extends between the distal end and the proximal end. A rectangular elongated recess 1452 is formed in the inner surface 1450. The recess 1452 is defined by two parallel elongated edges 1456, 1458. Elongated edges 1456, 1458 are parallel to each and offset parallel to the longitudinal axis extending centrally through the interior bore of the dilator 1400a in the closed position. Recess 1452 is further defined by short edges 1460, 1462 which are perpendicular to the ends of edges 1456, 1458. In one particular embodiment, the transversely aligned length of edges 1462 is less than the longitudinally aligned length of edges 1456, 1458. In one particular embodiment, the longitudinally aligned length of edges 1456, 1458 is in a range from about 7 to about 12 times greater than the transversely aligned length of edges 1460, 1462.

A high friction component 1454 is disposed within the recess 1452. In one particular embodiment the high friction component is flexible so as to flexibly conform with the radius of a curvature of the concavely curved inner surface 1450a. The term high friction with respect to the component 1454 refers to a material that is used to fabricate component 1454 that establishes a higher coefficient of friction relative to the exterior surface of the endoscope than the smooth or bare portion of the inner surface 1450a. As will be shown below in FIG. 17B, the high friction component 1454 is configured to engage an exterior surface of the body of the endoscope and frictionally interfere with the same in order to preclude relative movement of the dilator 1400a and the endoscope along the longitudinal axis.

Regarding the high friction component 1454, some exemplary materials that may be used to fabricate the high friction component 1454 may include a high-temperature silicone rubber, approximately 1/32" thick, clear, durometer 40A. Further, while the high friction component 1454 is shown as a rectangular and at least semi-flexible component inserted into the rectangular recess 1452, it is possible for other embodiments of dilators to have a high friction component sprayed on or otherwise adhered to the interior surface 1450 of one or both parts of the dilator. In this scenario, the dilator would be substantially continuous between the proximal end and distal end and adhered in substantially continuous contact. Some exemplary spray on high friction components may be sprayable polymers that cure to form a synthetic rubber texture along the inner surface 1450 of each part of the dilator. Alternatively, the high-friction component 1454 may be formed from a suction cup tape or a biocompatible sandpaper-like tape.

With continued reference to FIG. 16A, a female portion of a connector is formed in the first part 1406a. Female connector 1464 defines a recess 1466 configured to releasably retain the male connector 1712 on the second part 1406b. Female connector 1464 includes a longitudinally extending ledge 1468 extending between transversely aligned end walls 1470, 1472.

Dilator 1400a further includes at least one pin or boss extension 1474 extending transversely outward from a sidewall 1479 in a similar direction as the male connector 1712. The pins 1474 are positioned distally from the male connector. The pins 1474 are configured to align and be inserted into corresponding and complementary recesses or depressions 1476 formed in the sidewall 1478 of the first part 1406a. In some embodiments, the pins 1474 and corresponding recess 1476 are used to align the parts together when moving the dilator from the open position towards the closed position. In other embodiments, the pins 1474 may be utilized to releasably connect the two parts together. In the dilator 1400a, there are two pins positioned distally from the male connector, however, it is to be understood that any number of pins used to align the parts together are entirely possible. Additionally, it would be possible to form one of the pins in a sidewall of the second part to align with another recess formed in the sidewall 1478 of the first part located proximally from the female connector 1464.

FIG. 16B depicts a dilator 1400b having similar components as dilator 1400a depicted in FIG. 16A. However, dilator 1400b does not include recess 1452 having the high friction component 1454 disposed therein. Rather, the inner surface 1450 is substantially smooth between the ridges at the respective distal and proximal ends of the dilator. This dilator 1400b could be coated with a high friction spray on or otherwise applied friction component (not shown). As discussed previously, some exemplary spray on or applied high friction components include a spray polymer effectuating the texture of natural rubber similar to that of Flex Seal® or PlastiDip®. However, other rubberized coatings such as Rust-Oleum® Leak Seal or Rust-Oleum® FlexiDip could be spray on applied or otherwise painted on to the interior surface 1450 of each respective part of the dilator 1400b.

FIG. 16C depicts an alternative embodiment of a dilator 1400c similar to that of dilator 1400a except that dilator 1400c is free of the ridges formed at the proximal and distal ends. Rather, the smooth and concave inner surface 1450 on each part extends substantially or entirely between the proximal and distal end of dilator 1400c.

Figure 17A:
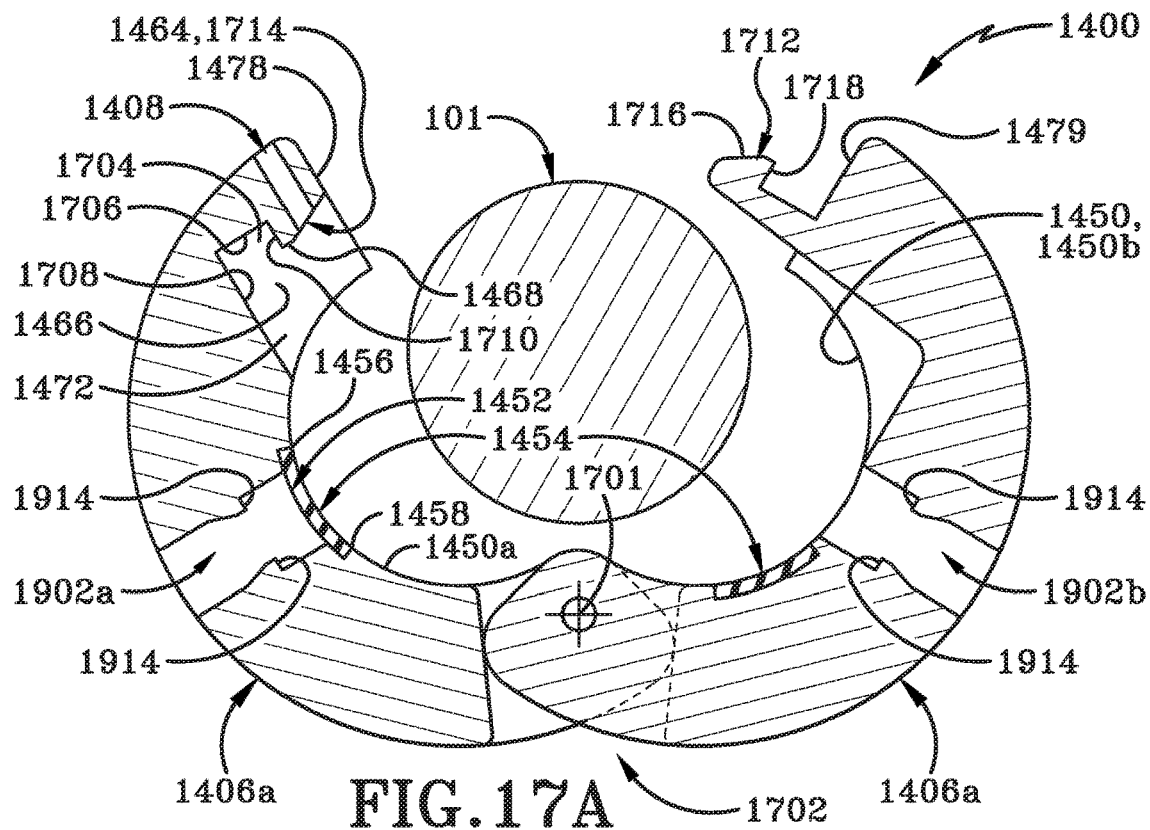
FIG. 17A is a cross section view taken along line 17A-17A in FIG. 16A depicting an endoscope position between two parts of the dilator in the open position.
Figure 17B:
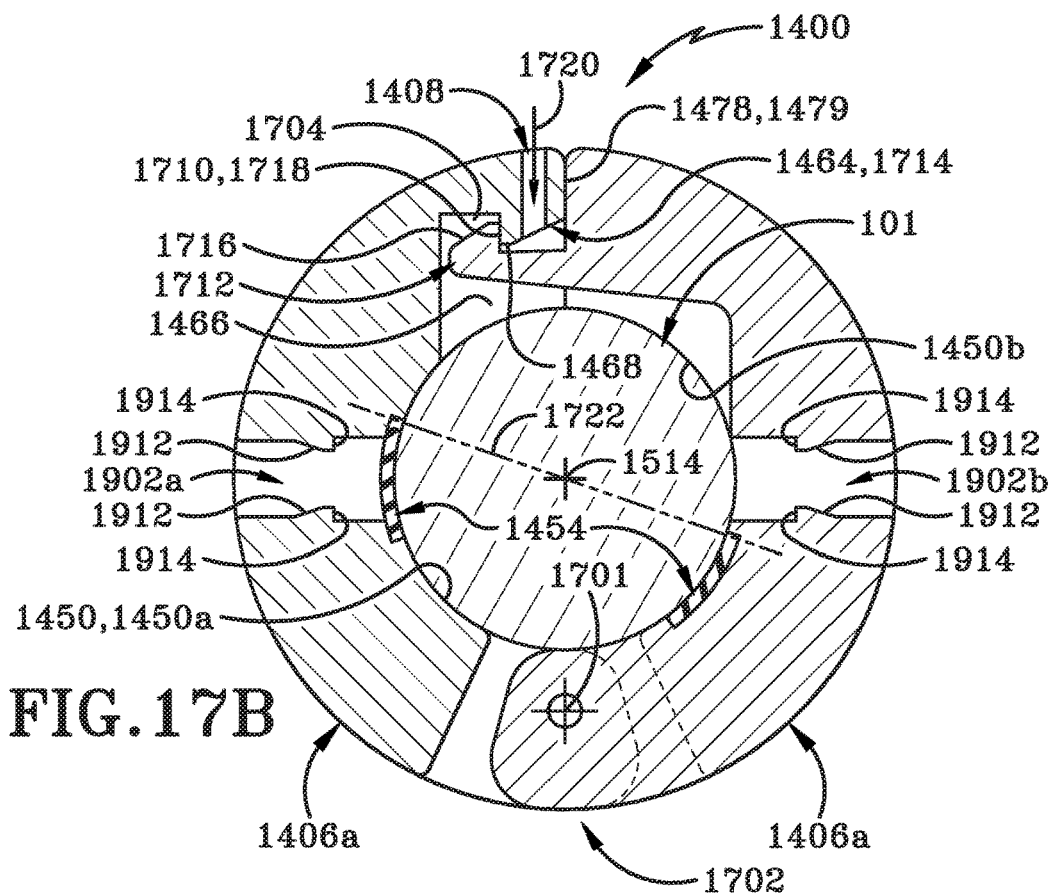
FIG. 17B is a cross section view similar to that of FIG. 17A but with the dilator in the closed position and circumscribing the body of the endoscope.

FIG. 17A depicts the open position of dilator 1400a and 1400c taken along line 17A-17A in FIG. 16A. The two parts are connected together via a hinge 1702 enabling two parts to pivot about the pivot axis 1701. The two parts may pivot to a closed position as depicted in FIG. 17B.

With continued referenced to FIG. 17A, the female connector 1464 defines an upper recess 1704 bound by a transverse wall 1706 and a vertical wall 1708 that is orthogonal to the transverse wall 1706. Recess 1704 is further bound by a short downwardly extending vertical wall 1710 that defines a lip configured to retain a complementary upwardly extending protrusion 1712 on the male connector on the second part of dilator 1400a. The longitudinally extending edge 1468 may be at a tapered angle to thereby define an angled wall 1714 that is configured to contact and urge in the downward direction a complementary angled wall 1716 on the protrusion 1712 of the male connector.

FIG. 17B depicts the dilator 1400a or 1400c in a closed position in which the male connector is releasably received in the female connector 1464 to secure the dilator in the closed position. When the male connector is matably connected with the female connector, a vertical wall 1718 on the protrusion 1712 of the male connector contacts the vertical wall 1710 of the female connector to create a secure connection of the two parts.

In order to release the mating connection of the first part and the second part, an elongated member or slot key may be inserted through the aperture 1408 as indicated by arrow 1720. The elongated member or slot key used to release the mating connection of the male and female connectors may contact the male connector to bias the male connector downwardly to release the engagement of wall 1710 with wall 1718. When the upper portion of the protrusion 1712 is below the bottom of short wall 1710, the two parts may be moved towards the open position.

With continued reference to FIG. 17B, it is shown that when the dilator 1400a is in the closed position, a portion of the first high friction insert or high friction component 1454 on the first part intersects a plane 1722 extending through the central longitudinal axis. A second high friction component formed on the insert into a corresponding recess in the second part of the dilator 1400a also intersects plane 1722. Accordingly, at least one portion of the high friction component 1454 on the first part is offset 180 degrees from the high friction component on the second part. While it is not necessary that the entire high friction component be offset from the other high friction component on the other part, it may be preferable for at least one portion of the high friction components to be offset 180 degrees from each other.

Figure 18A:
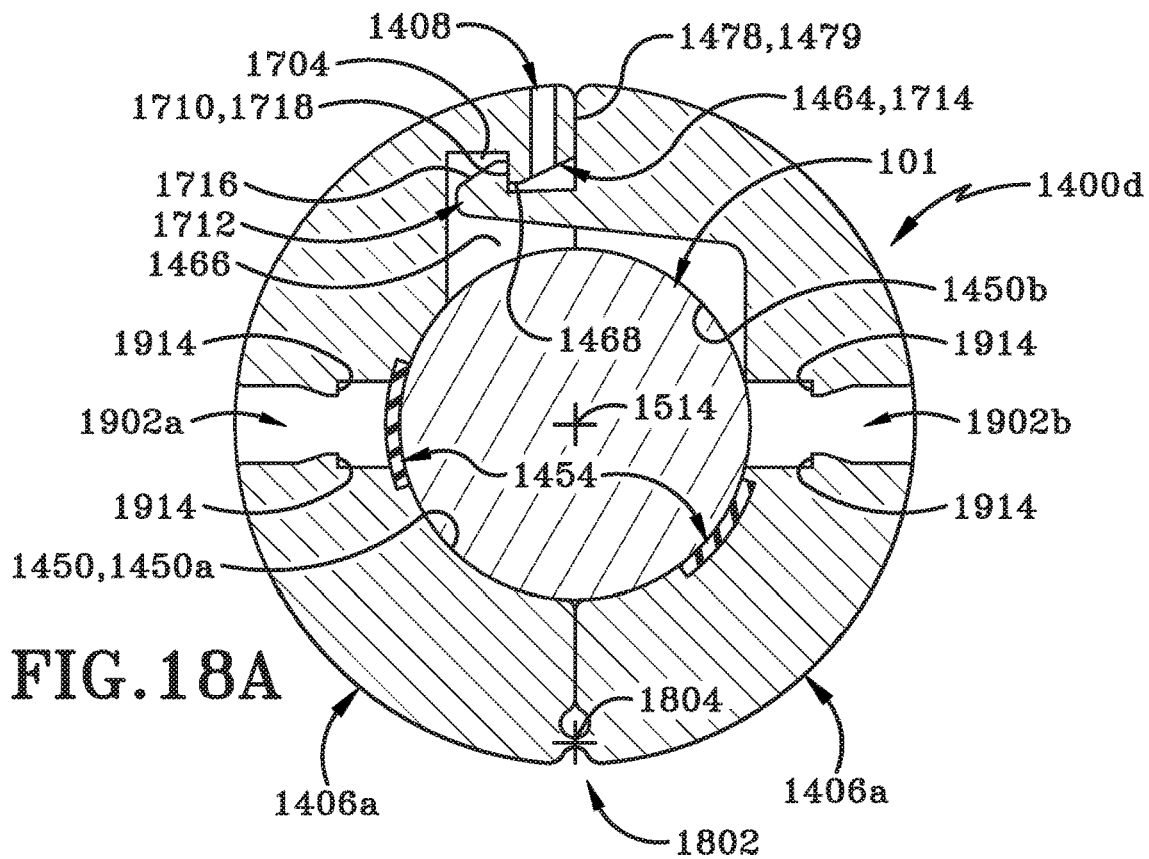
FIG. 18A is a cross section view of a dilator circumscribing an endoscope and the dilator having a living hinge or live hinge between the two halves of the dilator.

FIG. 18A depicts an alternative embodiment of a dilator 1400d as shown in cross section. Dilator 1400d utilizes a living hinge 1802 to define a hinge axis 1804. Hinge axis 1804 is offset parallel to the longitudinal central axis of the dilator 1400d. One advantage of using a living hinge 1802, according to an exemplary and non-limiting aspect of the present disclosure, is that the two parts may be formed as a unitary and unibody monolithic member thus eliminating the need for an additional component of a pin to effectuate the pin axis or hinge axis about which the two parts pivot to move the dilator between its open and closed positions.

Figure 18B:
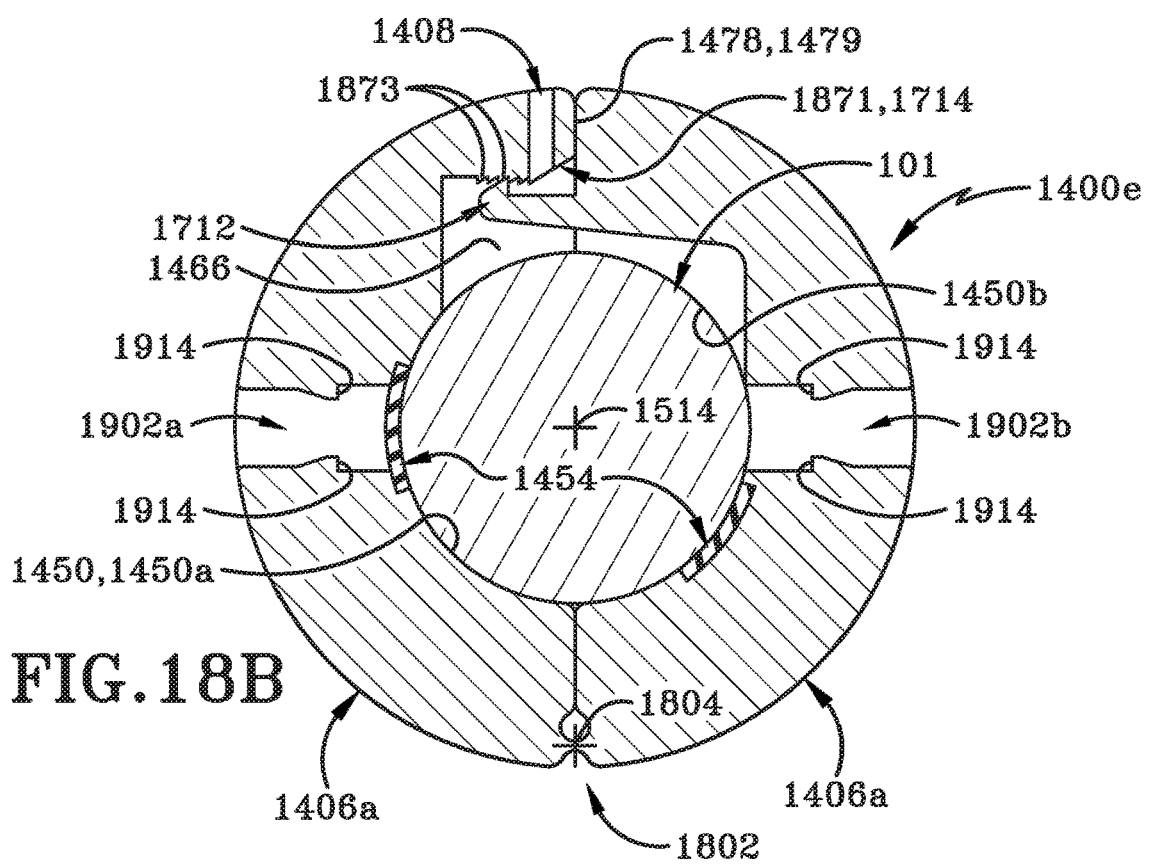
FIG. 18B is a cross section view of a dilator circumscribing an endoscope having a single-direction adjustable tightness releasable connection that is operable similar to a zip-tie.

FIG. 18B depicts an alternative embodiment of a dilator 1400e as shown in cross section. Dilator 1400e similarly uses the living hinge 1802 but has a closure that is single-direction adjustable located approximately 180 degrees from the hinge 1802. A single-direction adjustable female connector 1871 having a plurality of teeth 1873 oriented to encourage the male connector 1712 to move in one direction but not in the other. The teeth 1873 are oriented to enable the ever increasing tightness of the connection but preclude or limit the ability of the male connector 1712 from loosening. Thus, the dilator 1400e of FIG. 18B has a releasable closure that is operationally similar to that of a conventional zip-tie.

Figure 19A:
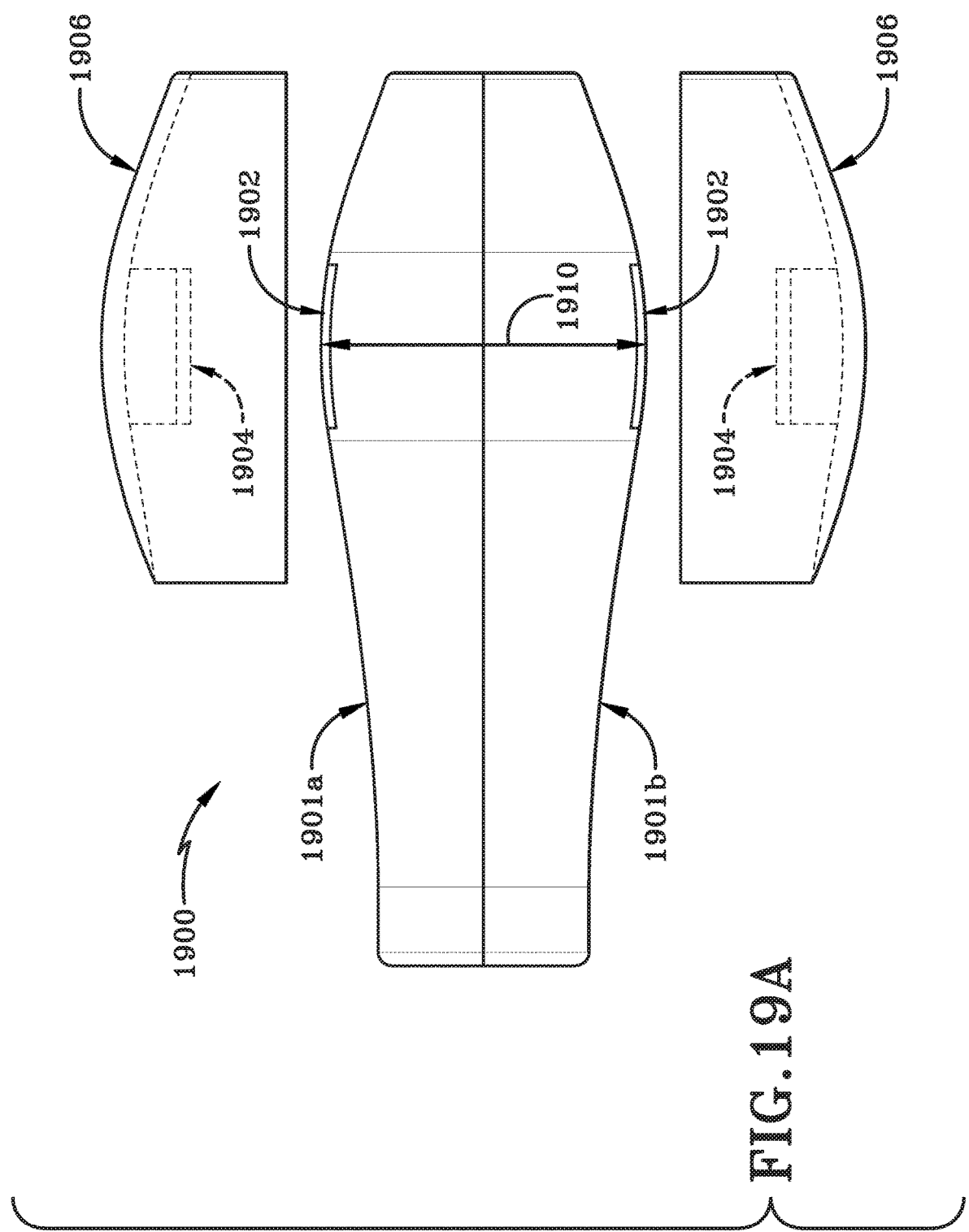
FIG. 19A is an exploded diagrammatic view of a dilator having covers or shrouds that are configured to connect with the dilator to increase the outer diameter thereof.
Figure 19B:
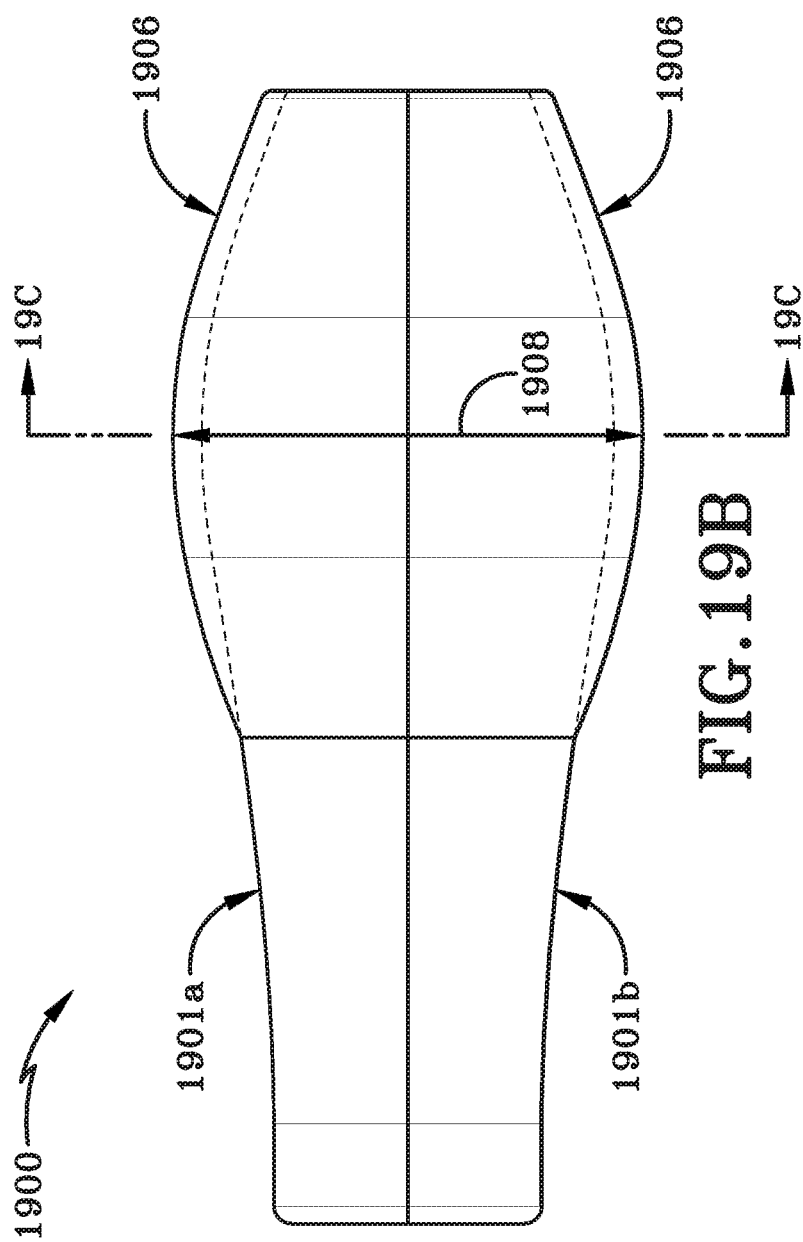
FIG. 19B is a diagrammatic view of the dilator of FIG. 19A with the covers attached to increase the outer diameter.
Figure 19C:
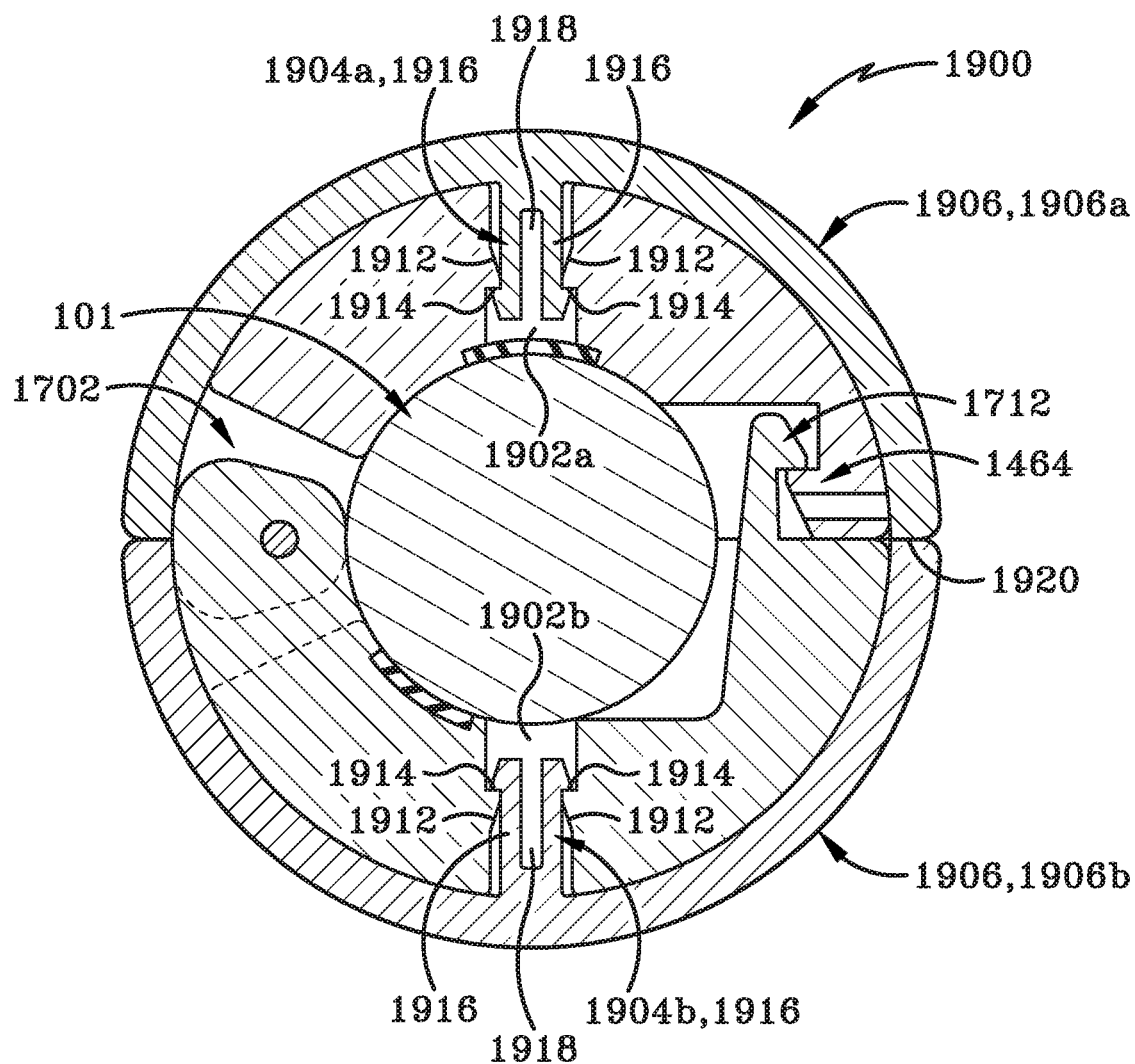
FIG. 19C is a cross section view taken along line 19C-19C in FIG. 19B depicting the covers connected to the outer surface of the dilator.

FIG. 19A, FIG. 19B, and FIG. 19C depict another exemplary dilator 1900 having similar features as other profiles of dilators described herein. Dilator 1900 may be formed with apertures 1902 extending through the sidewalls in each of the respective parts 1901a, 1901b of dilator 1900. The apertures configured to receive a tab or insert 1904 on a cover or shroud 1906 to releasably connect the shroud 1906 to the exterior surface of the dilator 1900 on each respective part, 1901a, 1901b.

FIG. 19B depicts a diagrammatic embodiment in which two shrouds or covers 1906 have been respectively connected to the first part 1901a and the second part 1901b to increase its maximum outer diameter measured through the apex region. Arrows 1908 indicate an increase in the diameter after having the two shrouds or covers 1906 respectively connected to the exterior surface of the dilator 1900. As stated previously with the other adjustable diameter dilators, the dilator 1900 may be used with a method of operation in which after inserting the dilator in its first state without covers through the stricture 777, the surgeon or gastroenterologist may inspect the stricture 777 and determine that it still needs further dilation. Thus, upon extracting the dilator through the esophagus and outwardly through the mouth, the surgeon or gastroenterologist may attach one or more additional covers 1906 to increase the exterior diameter of the dilator 1900 to a preferred diameter. In one particular embodiment, each cover is associated with increasing the diameter by 3 French. Thus, if the original diameter 1910 of dilator 1900 is 51 French and the surgeon or gastroenterologist determines that the stricture needs to be dilated to 54 French, then the surgeon or gastroenterologist may connect one cover 1906 to one part of the dilator 1900. Thus, the dilator would be increased in exterior diameter to 54 French (the base diameter of 1910 of 51 French plus the diameter increasing dimension of 3 French of one cover 1906). If after a second evaluation or determination that the stricture 777 needs to be further increased to a diameter of 57 French, the process may be repeated and a second cover may be attached to the other part of the dilator. Thus, the maximum diameter of the dilator 1900 with the two covers 1906 attached would be 57 French as indicated by diameter 1908. More particularly, adding a second cover 1906 increases the exterior diameter 1908 of dilator 1900 to 57 French by adding an extra 3 French diameters to the previous assembly having a diameter of 54 French.

As depicted in FIG. 19C, each cover 1906 is shown as connected to the external surface of the dilator. More particularly, a first cover 1906a is connected to the first part through its tab 1904a being received with an aperture 1902a. In one particular embodiment, aperture 1902a may be defined by a radially aligned wall 1912 that tapers inwardly and defines a ledge 1914. Tab 1904a may include two extending arms 1916 having enlarged ends that are configured to flex inwardly based on a gap 1918 separating the two arms 1916. The tapered wall 1912 encourages the enlarged ends of the arms 1916 to move inwardly towards each other as the ends of the arms move past a narrowed region of the aperture 1902a and then expand back outwardly such that the enlarged ends of the arms 1916 are retained by the ledge 1914 to releasably secure the cover 1906a to the exterior surface of the first part of dilator 1900. A similar configuration is utilized to effectuate the connection of the second cover of 1906b to the second part of dilator 1900. The second tab 1904b is inserted into a corresponding aperture 1902b on the second part and has the similar tapered wall 1912, ledge 1914, two arms 1916, and the gap 1918. In one particular embodiment, the apertures are radially aligned 180 degrees from each other so that the ends of the covers align to form unions 1920 that are oriented 90 degrees from each respective aperture 1902a, 1902b.

It is to be clearly understood that the internal geometric configurations of the lumen of any dilator embodiment can be fabricated with any of the outer geometric configurations of the dilator. So for example, the internal configuration of dilator 1400 may be used in combination with any other dilator external configuration or profile shape. Further, each instance or reference to the term "part" is meant to provide support and have the same meaning as the term "side segment" when used in the appended claims. Stated otherwise, the term "part" may be used interchangeably with the term "side segment" throughout this disclosure.

Figure 20:
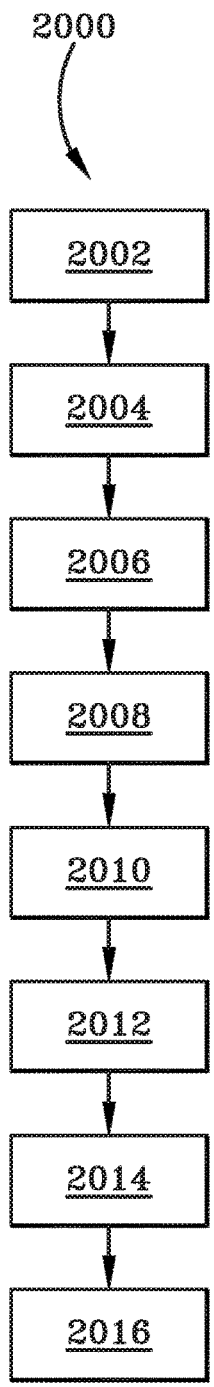
FIG. 20 is a flow chart depicting an exemplary method in accordance with one aspect of the present disclosure.

FIG. 20 depicts an operational method for some of the exemplary dilators described herein generally at 2000.

Method 2000 includes providing a first dilator formed from two parts that are moveable relative to each other between an open position and closed position, which is shown generally at 2002. Method 2000 includes opening the first dilator to the open position, which is shown generally at 2004. Method 2000 includes disposing an elongated member adjacent an interior surface of one of the two parts, wherein a length of the elongated member extends distally from a distal end of the first dilator, which is shown generally at 2006. Method 2000 includes securing the first dilator to the elongated member by moving the two parts to the closed position while retaining the elongated member between the two parts such that the first dilator does translate relative a longitudinal axis of the elongated member, which is shown generally at 2008. Method 2000 includes moving the elongated member and secured first dilator through a lumen formed in a tubular body, which is shown generally at 2010. Method 2000 includes approaching a narrowed region of the lumen with a distal end of the elongated member, which is shown generally at 2012. Method 2000 includes first, moving the length of the elongated member that extends distally from a distal end of the first dilator through the narrowed region of the lumen, and then moving the first dilator through the narrowed region of the lumen, which is shown generally at 2014. Method 2000 includes dilating the narrowed region of the lumen as the first dilator passes therethrough to increase a diameter of the narrowed region, wherein the narrowed region has a larger diameter after the first dilator has been passed therethrough than prior to moving the first dilator through the narrowed region of the lumen, which is shown generally at 2016.

Method 2000 or another exemplary method may further include removing the first dilator and elongated member from the lumen; moving the two parts from the closed position; and disconnecting the elongated member from the first dilator. Method 2000 or another exemplary method may further include wherein prior to disposing the elongated member adjacent the interior surface of one of the two parts in the open position comprises: inserting the elongated member in the lumen formed in the tubular body without the first dilator connected to the elongated member; inspecting the narrowed region of the lumen; extracting the elongated member from the lumen, and then disposing the elongated member adjacent the interior surface of one of the two parts. Method 2000 or another exemplary method may further include securing the first dilator to the elongated member in a range from about 20 cm to about 30 cm from a terminal end of the elongated member. Method 2000 or another exemplary method may further include dilating the narrowed region of the lumen to a diameter in a range from about 42 French to about 60 French after having passed the first dilator therethrough. Method 2000 or another exemplary method may further include increasing an external diameter of the first dilator after having passed through the narrowed region at least once. Method 2000 or another exemplary method may further include attaching a cover to an outer surface of the first dilator to increase the external diameter of the first dilator. Method 2000 or another exemplary method may further include expanding an outer surface of the first dilator to increase the external diameter of the first dilator, wherein expanding the outer surface is accomplished by rotating a threaded component about a longitudinal axis of the first dilator to cause linear translation thereof to push the outer surface radially outward relative to the longitudinal axis. Method 2000 or another exemplary method may further include dilating the narrowed region of the lumen a second time after having increased the external diameter of the first dilator.

Figure 21:
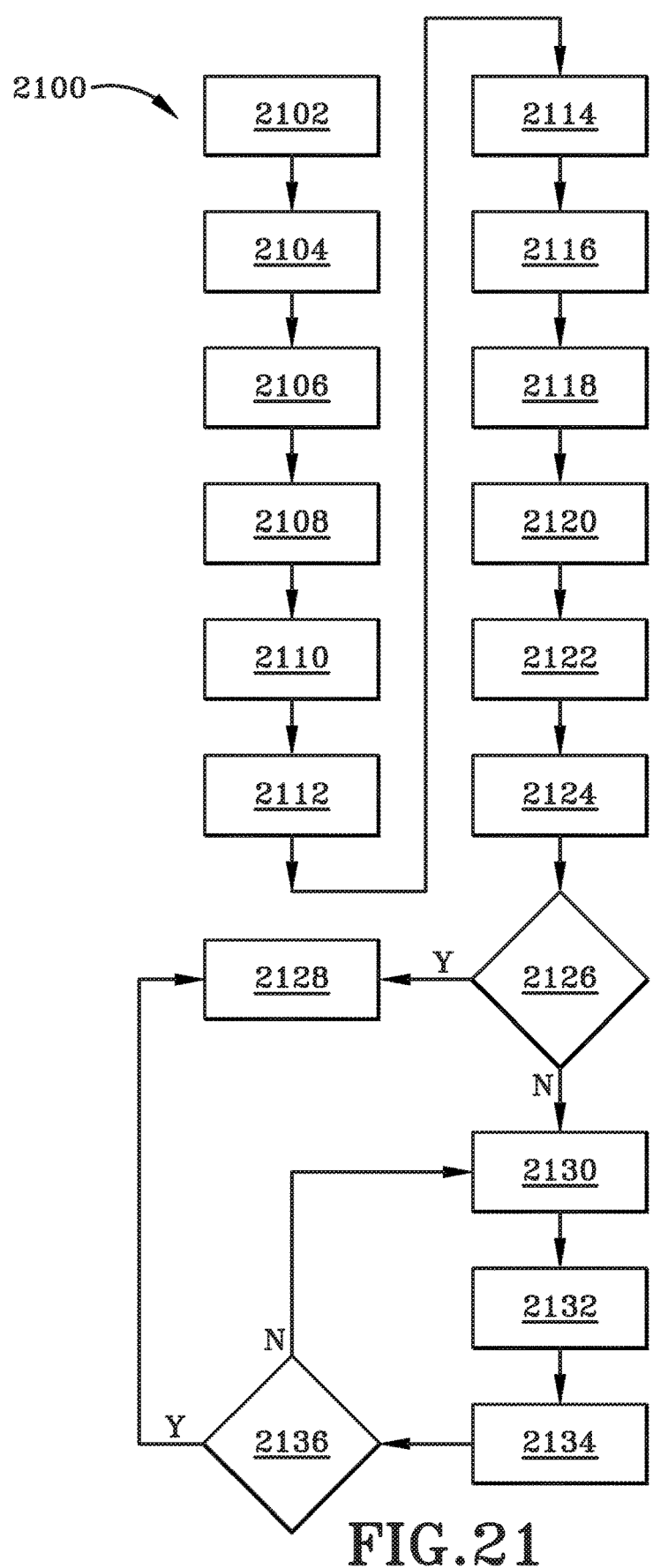
FIG. 21 is a flow chart depicting another exemplary method in accordance with another aspect of the present disclosure.

FIG. 21 depicts another exemplary operational method of the present disclosure generally at 2100. Method 2100 may include inserting a portion of an endoscope into an esophagus, which is shown generally at 2102. Method 2100 may include passing a distal end of the endoscope through the esophagus towards a stomach, which is shown generally at 2104. Method 2100 may include approaching the distal end of the endoscope towards a stricture, which is shown generally at 2106. Method 2100 may include inspecting the stricture and approximating a diameter of the stricture, which is shown generally at 2108. Method 2100 may include extracting a portion of the endoscope from the esophagus while leaving the distal end of the endoscope intubated within the esophagus, which is shown generally at 2110. Method 2100 may include connecting a dilator (e.g., any of the dilators discussed herein) to the extracted portion of the endoscope while the distal end of the endoscope remains intubated within the esophagus, which is shown generally at 2112. Method 2100 may include passing the dilator connected to the endoscope through the esophagus, which is shown generally at 2114. Method 2100 may include, for or a second time, approaching the distal end of the endoscope towards the stricture, which is shown generally at 2116. Method 2100 may include passing the distal end of the endoscope through the stricture and into the stomach, which is shown generally at 2118. Method 2100 may include passing the dilator through the stricture and into the stomach to dilate the stricture to have a greater diameter than prior to the dilator therethrough, wherein as the dilator is passed through the stricture, the distal end of the endoscope advances farther into the stomach, which is shown generally at 2120. Method 2100 may include extracting the dilator through the stricture in an opposite direction, which is shown generally at 2122. Method 2100 may include, for a second time, inspecting the stricture after having been dilated by the dilator, which is shown generally at 2124. Method 2100 may include confirming that the stricture has been dilated to a preferred diameter, which is shown generally at 2126. Confirming that the stricture has been dilated to the preferred diameter has two results (i.e., Yes ("Y") or No ("N")). Wherein, if the stricture has been dilated to the preferred diameter (i.e., Yes), then method 2100 includes removing the dilator and endoscope from the esophagus, which is shown generally at 2128.

If, at 2126, the stricture has not been dilated to the preferred diameter (i.e., No), then, method 2100 may include removing the dilator and the portion of the endoscope from the esophagus while leaving the distal end of the endoscope intubated within the esophagus, which is shown generally at 2130. Method 2100 may further include adjusting an external diameter of the dilator while the dilator is outside of the esophagus, which is shown generally at 2132. Method 2100 may further include moving the dilator through the stricture for a second time after having the external diameter adjusted, which is shown generally at 2134. Then, the stricture may be reevaluated to confirm whether it has been dilated to the preferred diameter, which is shown generally at 2136. If, at 2136, the stricture has been dilated to the preferred diameter (i.e., Yes), then the dilator is removed at 2128. If, at 2136, the stricture has not been dilated to the preferred diameter (i.e., No), then steps 2130, 2132, and 2134 may be repeated until the diameter of the stricture is dilated to the preferred diameter so the dilator may be removed at 2128.

Method 2100 or another exemplary method may further include, wherein connecting the dilator to the extracted portion of the endoscope includes: moving a first part of the dilator to an open position; positioning the extracted portion of the endoscope adjacent an inner surface of the dilator; moving the first part of the dilator to a closed position; and releasably securing the dilator in the closed position. Method 2100 or another exemplary method may further include wherein connecting the dilator to the extracted portion of the endoscope further includes: positioning the dilator a distance in a range from about 20 cm to about 30 cm from the distal end of the endoscope. Method 2100 or another exemplary method may further include wherein connecting the dilator to the extracted portion of the endoscope further includes: contacting ridges formed in a distal end of the first part with an exterior surface of the extracted portion of the dilator. Method 2100 or another exemplary method may further include wherein connecting the dilator to the extracted portion of the endoscope further includes: releasably securing the first part to a second part of the dilator via a snap-fit connection. Method 2100 or another exemplary method may further include wherein connecting the dilator to the extracted portion of the endoscope further includes: aligning a first high-friction component adjacent or on the inner surface of the first part 180 degrees from a second high-friction component adjacent or on an inner surface of a second part of the dilator. Method 2100 or another exemplary method may further include wherein connecting the dilator to the extracted portion of the endoscope further includes: pivoting the first part about a hinged relative to a second part to releasably secure the dilator in the closed position. Method 2100 or another exemplary method may further include wherein connecting the dilator to the extracted portion of the endoscope further includes: minimizing an internal diameter of the dilator measured between complementary inner surfaces on the first part and a second part, wherein the internal diameter is minimized in the closed position and in the inner surfaces are in direct contact with an exterior surface of the extracted portion of the endoscope. Method 2100 or another exemplary method may further include wherein connecting the dilator to the extracted portion of the endoscope further includes: frictionally engaging the inner surface of the dilator to an exterior surface of the extracted portion of the dilator. Method 2100 or another exemplary method may further include wherein connecting the dilator to the extracted portion of the endoscope further includes: frictionally engaging a component formed from a different material than the first part of the dilator with the exterior surface of the extracted portion of the dilator. Method 2100 or another exemplary method may further include passing an apex of an outer surface of the dilator through the stricture, wherein the apex is disposed a distance in a range from about 20 cm to about 30 cm from the distal end of the endoscope.

Advantageously, because the dilators described herein are directly attached to an endoscope, nearly immediate visualization of the dilated stricture can be provided. Further, because the tip of the scope can remain in the esophagus throughout the dilation process (i.e., even when changing out the dilator for a larger size, expanding the dilators, or imaging in between expansions), the esophagus does not need to be repeatedly intubated during the process.

The dilators described herein can advantageously be single-use and disposable. This can reduce the risk of infection and the need for cleaning and sterilization. It can decrease the risk of soiling the operating field, and eliminate the risk of trauma to the staff with guidewires (that are often used with other dilation systems). Safety and efficacy of esophageal dilation is also increased using the dilators described herein, as feedback from tactile sensation can be obtained during insertion of the endoscope so as to avoid perforating by using excessive force.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Therefore, the foregoing description is provided primarily for exemplary purposes and should not be interpreted to limit the scope of the invention as it is set forth in the claims.

All definitions, a defined and used herein, should be understood to control over dictionary definitions, definitions in documents incorporated by reference, and/or ordinary meanings of the defined terms.

The articles "a" and "an," as used herein in the specification and in the claims, unless clearly indicated to the contrary, should be understood to mean "at least one." The phrase "and/or," as used herein in the specification and in the claims (if at all), should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Spatially relative terms, such as "under", "below", "lower", "over", "upper", "above", "behind", "in front of", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal", "lateral", "transverse", "longitudinal", and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed herein could be termed a second feature/element, and similarly, a second feature/element discussed herein could be termed a first feature/element without departing from the teachings of the present invention.

An embodiment is an implementation or example of the present disclosure. Reference in the specification to "an embodiment," "one embodiment," "some embodiments," "one particular embodiment," or "other embodiments," or the like, means that a particular feature, structure, or characteristic described in connection with the embodiments is included in at least some embodiments, but not necessarily all embodiments, of the invention. The various appearances "an embodiment," "one embodiment," "some embodiments," "one particular embodiment," or "other embodiments," or the like, are not necessarily all referring to the same embodiments.

If this specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Additionally, any method of performing the present disclosure may occur in a sequence different than those described herein. Accordingly, no sequence of the method should be read as a limitation unless explicitly stated. It is recognizable that performing some of the steps of the method in a different order could achieve a similar result.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of various embodiments of the disclosure are examples and the disclosure is not limited to the exact details shown or described.

What is claimed:

1. A dilator for connection with an endoscope to dilate a stricture, the dilator comprising:
    a first side segment; and
    a second side segment;
    wherein the first side segment and the second side segment are adapted to receive a portion of the endoscope therebetween;
    wherein the first side segment and the second side segment are connected together to form a closed position and collectively include;
        a proximal end spaced from a distal end defining a longitudinal axis, wherein the distal end is configured to pass through the stricture before the proximal end;
        an outer surface extending from the proximal end to the distal end;
        a distal portion of the outer surface that is angled relative to the longitudinal axis at a first angle;
        a proximal portion of the outer surface that is angled relative to the longitudinal axis at a second angle;
        an apex of the outer surface intermediate the proximal portion and the distal portion of the outer surface; and
        an inner surface adapted to circumscribe at least a portion of an exterior of the endoscope; and
    the dilator comprising:
        a frustoconical first surface on the distal portion of the outer surface that extends between a first terminal end and the apex, and a frustoconical second surface on the proximal portion of the outer surface that extends between a second terminal end and the apex; or
        a curved first surface on the distal portion of the outer surface that extends between a first terminal end and the apex, and a curved second surface on the proximal portion of the outer surface that extends between a second terminal end and the apex.

2. The dilator of claim 1, wherein the first side segment and the second side segment move between an open position and the closed position, and when the first side segment and the second side segment are in the open position, a portion of the endoscope is moveable into engagement with one of the first side segment and the second side segment, and when the first side segment and the second side segment are in the closed position, the first side segment and the second side segment circumscribe and are carried by the portion of the endoscope.

3. The dilator of claim 2, further comprising:
    a first recess formed in an inner surface of the first side segment; and
    a first insert shaped complementary to the first recess and disposed within the first recess, and wherein the first insert is configured to frictionally engage an exterior of the endoscope.

4. The dilator of claim 3, further comprising:
    a second recess formed in the inner surface of the second side segment;
    a second insert shaped complementary to the second recess and disposed within the second recess, and the second insert is configured to frictionally engage the exterior of the endoscope when the dilator in the closed position.

5. The dilator of claim 4, wherein the first recess and the second recess are longitudinally elongated.

6. The dilator of claim 4, wherein the first recess is rectangular.

7. The dilator of claim 4, wherein the first recess is offset 180 degrees relative to a longitudinal axis of the dilator from the second recess when the dilator is in the closed position.

8. The dilator of claim 1, further comprising:
    a component connected to an inner surface of the first side segment that has a higher coefficient of friction relative to the exterior of the endoscope than the inner surface.

9. The dilator of claim 8, wherein the component is spray-on applied to the inner surface.

10. The dilator of claim 1, further comprising:
    a high-friction layer disposed between an inner surface of the first side segment and an exterior of the endoscope when the dilator is in a closed position.

11. The dilator of claim 1, further comprising respective inner surfaces of the first side segment and the second side segment that are shaped complementary to an exterior surface of the endoscope.

12. The dilator of claim 1, further comprising:
a hinge, wherein the first side segment defines a first side of the hinge and the second side segment defines a second side of the hinge;
wherein the first side and the second side of the hinge are coupled together to pivotably connect the first side segment and the second side segment together, wherein the first side segment and the second side segment pivot between an open position and the closed position via the hinge.

13. The dilator of claim 12, further comprising:
a first connector on the first side segment opposite the hinge; and
a second connector on the second side segment opposite the hinge;
wherein the first connector and the second connector effectuate a releasable connection between the first side segment and the second side segment, and when the dilator is in the open position, the first connector and the second connector are disconnected and when the dilator is in the closed position, the first connector and the second connector are connected.

14. The dilator of claim 1, where the first angle of the distal portion is smaller than the second angle of the proximal portion, such that the distal portion of the outer surface is longitudinally elongated relative to the proximal portion of the outer surface.

15. The dilator of claim 1,
wherein the frustoconical first surface is longer than the frustoconical second surface.

16. The dilator of claim 1, further comprising:
wherein the apex is disposed closer to the proximal end of the dilator than to the distal end.

17. The dilator of claim 1,
wherein the curved first surface is longer than the curved second surface.

18. A dilator for connection with an endoscope to dilate a stricture,
the dilator comprising:
a first side segment; and
a second side segment:
wherein the first side segment and the second side segment are adapted to receive a portion of the endoscope therebetween;
wherein the first side segment and the second side segment are connected together to form a a close position and collectively include;
a proximal end spaced from a distal end defining a longitudinal axis, wherein the distal end is configured to pass through the stricture before the proximal end;
an outer surface extending from the proximal end to the distal end;
a distal portion of the outer surface that is angled relative to the longitudinal axis at a first angle;
a proximal portion of the outer surface that is angled relative to the longitudinal axis at a second angle;
an apex of the outer surface intermediate the proximal portion and the distal portion of the outer surface; and
an inner surface adapted to circumscribe at least a portion of an exterior of the endoscope;

the dilator further comprising:
an aperture formed in the outer surface of the first side segment; and
a supplemental component sized for insertion into the aperture formed in the outer surface of the first side segment to increase an outer diameter of the dilator when the dilator is in the closed position.

19. A dilator to releasably connect with an endoscope to dilate a stricture as the dilator that is releasably connected to a portion of a cylindrical body of the endoscope passes through the stricture, the dilator including:
a first part and a second part that are releasably connected together to move the dilator between an open position and a closed position configured to enable the endoscope to be positioned between a first element and a second element, wherein when the first part and the second part are in the closed position, an inner surface frictionally secures the dilator to a portion of the cylindrical body of the endoscope and when the first part and the second part are in the open position, the inner surface does not frictionally secure the dilator to the portion of the cylindrical body of the endoscope;
wherein the first part and the second part are connected together to form a closed position and collectively include:
a proximal end spaced from a distal end defining a longitudinal axis, wherein the distal end is configured to pass through the stricture before the proximal end;
an outer surface extending from the proximal end to the distal end;
a distal portion of the outer surface that is angled relative to the longitudinal axis at a first angle;
a proximal portion of the outer surface that is angled relative to the longitudinal axis at a second angle;
an apex of the outer surface intermediate the proximal portion and the distal portion of the outer surface; and
an inner surface adapted to circumscribe at least a portion of an exterior of the endoscope; and
the dilator comprising:
a frustoconical first surface on the distal portion of the outer surface that extends between a first terminal end and the apex, and a frustoconical second surface on the proximal portion of the outer surface that extends between a second terminal end and the apex; or
a curved first surface on the distal portion of the outer surface that extends between a first terminal end and the apex, and a curved second surface on the proximal portion of the outer surface that extends between a second terminal end and the apex.

20. The dilator of claim 19, further comprising:
a component on or adjacent the inner surface of the dilator to frictionally engage the portion of the cylindrical body of the endoscope.

* * * * *